US008017388B2

(12) United States Patent
Goletz et al.

(10) Patent No.: US 8,017,388 B2
(45) Date of Patent: Sep. 13, 2011

(54) TUMOUR CELL LINES AND USES THEREOF

(75) Inventors: Steffen Goletz, Glienicke (DE); Hans Baumeister, Berlin (DE); Marion Schlangstedt, Berlin (DE); Ute Schöber, Berlin (DE)

(73) Assignee: Glycotope GmbH, Berlin (DE)

( * ) Notice: Subject to any disclaimer, the term of this patent is extended or adjusted under 35 U.S.C. 154(b) by 458 days.

(21) Appl. No.: 10/568,098

(22) PCT Filed: Aug. 18, 2004

(86) PCT No.: PCT/EP2004/009281
§ 371 (c)(1),
(2), (4) Date: Jun. 20, 2006

(87) PCT Pub. No.: WO2005/017130
PCT Pub. Date: Feb. 24, 2005

(65) Prior Publication Data
US 2006/0292129 A1 Dec. 28, 2006

(30) Foreign Application Priority Data
Aug. 18, 2003 (EP) .................................. 03018576

(51) Int. Cl.
*C12N 5/00* (2006.01)
(52) U.S. Cl. ....................................................... 435/325
(58) Field of Classification Search .................. 435/325; 514/1
See application file for complete search history.

(56) References Cited

U.S. PATENT DOCUMENTS

| | | | |
|---|---|---|---|
| 4,931,275 A | 6/1990 | Shinitzky et al. | |
| 5,948,646 A | 9/1999 | Srivastava | |
| 5,961,979 A | 10/1999 | Srivastava | |
| 6,168,793 B1 | 1/2001 | Srivastava | |
| 6,984,384 B1 | 1/2006 | Subjeck et al. | |
| 7,268,120 B1* | 9/2007 | Horton et al. ................ | 514/44 |
| 7,595,192 B2 | 9/2009 | Goletz et al. | |
| 2006/0292129 A1 | 12/2006 | Goletz et al. | |

FOREIGN PATENT DOCUMENTS

| | | |
|---|---|---|
| WO | WO 94/29469 | 12/1994 |
| WO | WO 97/00957 | 1/1997 |
| WO | WO 9740182 A | 10/1997 |
| WO | WO 99/29834 A | 6/1999 |
| WO | WO 03/023023 | 3/2003 |
| WO | WO 2004009632 A | 1/2004 |
| WO | WO 2004018659 A | 3/2004 |

OTHER PUBLICATIONS

Jaget et al., , Journal of Clinical Oncology, vol. 20, Issue 18 (Sep.), 2002: 3872-3877, 2002 American Society for Clinical Oncology.*
Czuczman et al., , Treatment of Patients With Low-Grade B-Cell Lymphoma With the Combination of Chimeric Anti-CD20 Monoclonal Antibody and CHOP Chemotherapy Journal of Clinical Oncology, vol. 17, Issue 1 (Jan.), 1999: 268-276.*
Carbone et al., Multistep and multifactorial carcinogenesis: when does a contributing factor become a carcinogen? Seminars in Cancer Biology vol. 14, Issue 6, Dec. 2004, pp. 399-405.*
Goletz et al., "Antigen: the "hidden" tumour antigen." Adv. Exp. Med. Bio/., 535:147-62 (2003).*
Benoist et al., Immunology Letters Studies on the susceptibility to NK-mediated lysis and the simultaneous expression of various surface molecules in anthracyclin-treated K562 cells and in four K562 cell clones , 1992, pp. 45-55.*
Hinoda et al., Primary structure of the variable regions of a monoclonal antibody MUSE11 recognizing the tandem repeat domain of a mucin core protein, MUC1 Journal of Clinical Laboratory Analysis vol. 7 Issue 2, pp. 100-104.*
Ichiyama et al., 2000, Journal of Institute of Aging and Medical pp. 18. Official translation.*
Suzuki Mutat Res 1997; pp. 75-82; Abstract.*
Böhm et al., "Carbohydrate Recognition on MUC1-Expressing Targets Enhances Cytoxicity of a T cell Subpopulation", *Scandinavian Journal of Immunology*, vol. 46, No. 1, pp. 27-34, XP-002323076 (1997).
Cao et al., "Immunodetection of Epithelial Mucin (MUC1, MUC3) and Mucin-associated Glycotopes (TF, Tn, and sialosyl-Tn) in Benign and Malignant Lesions of Colonic Epithelium: Apolar Localization Corresponds to Malignant Transformation", *Virchows Archiv*, vol. 431, No. 3, pp. 159-166, XP-002323077, (1997).
Duk et al., "Purification of Human Anti-TF (Thomsen-Friedenreich) and Anti-Tn Antibodies by Affinity Chromatography on Glycophorin A Derivatives and Characterization of the Antibodies by Microtiter Plate ELISA", *Archivum Immunologiae et Therapiae Experimentalis*, vol. 46, No. 2, pp. 69-77, XP-008045186, (1998).
Gollasch et al., "Identification of Immunogenic Peptide-Mimics for the Thomsen-Friedenreich-Glycoantigen", *Annals of Hematology*, Berlin, DE, vol. 77, No. suppl. 2, p. S84, XP-000960533, (1998).
Karsten et al., "Enhanced Binding of Antibodies to the DTR Motif of MUC1 Tandem Repeat Peptide is Mediated by Site-Specific Glycosylation", *Cancer Research, American Association for Cancer Research*, Baltimore, MD, US, vol. 58, No. 12, pp. 2541-2549, XP-002112486, (Jun. 15, 1998).

(Continued)

*Primary Examiner* — Maria Leavitt
(74) *Attorney, Agent, or Firm* — Hamilton, Brook, Smith & Reynolds, P.C.

(57) ABSTRACT

The present invention relates to a cell line selected from the group consisting of (a) a cell line denominated NM-F9 having the DSMZ accession number DSM ACC2606; (b) a cell line denominated NM-D4 having the DSMZ accession number DSM ACC2605; and subclones of (a) or (b). Additionally, the present invention provides a lysate of the cell lines or a molecule or mixture of molecules obtained from these cell lines as well as dendritic cells loaded with said lysate, co-cultivated or fused with cells from the cell lines, or a molecule or mixture of molecules obtained from these cell lines of the present invention. Moreover compositions, preferably pharmaceutical or vaccine compositions are provided which comprise the cell lines, lysate, molecules, mixture of molecules or dendritic cells of the present invention. In another aspect the present invention relates to methods for producing the aforementioned compositions. Furthermore, methods and uses for vaccination against or treatment or prevention of cancers and/or tumourous diseases are provided.

13 Claims, 7 Drawing Sheets

OTHER PUBLICATIONS

Figure 1:
Figure 1:
Figure 1:
Figure 1:
Figure 1:
Figure 1:
Figure 1:
Figure 1:
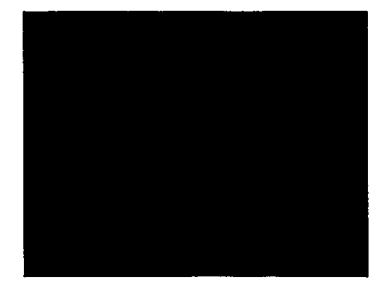
Figure 1:
Figure 1:

Kunz, "Synthetic Glycopeptides for the Development of Tumour-selective Vaccines", *Journal of Peptide Science: an Official Publication of the European Peptide Society*, vol. 9, No. 9, pp. 563-573, XP-00845163, (Sep. 2003).

Anderson. "Human Gene Therapy". Science, vol. 256, 1992, pp. 808-813.

Brummelkamp, et al. "A System for Stable Expression of Short Interfering RNAs in Mammalian Cells". Science, vol. 296, 2002, pp. 550-553.

Elbashir, et al. "Duplexes of 21-nucleotide RNAs mediate RNA interference in cultured mammalian cells". Nature, vol. 411, 2001, pp. 494-498.

Isner, et al. "Clinical evidence of angiogenesis after arterial gene transfer of phVEGF165 in patient with ischaemic limb". The Lancet, vol. 348, 1996, pp. 370-374.

Novina, et al. "siRNA-directed inhibition of HIV-1 infection". Nature Medicine, vol. 8, No. 7, 2002, pp. 681-686.

Ohyama, et al. "Dual roles of sialyl Lewis X oligosaccharides in tumor metastasis and rejection by natural killer cells". The EMBO Journal, vol. 18, No. 6, 1999, pp. 1516-1525.

Ohyama, et al. "Natural killer cells attack tumor cells expressing high levels of sialyl Lewis x oligosaccharides". PNAS, vol. 99, No. 21, 2002, pp. 13789-13794.

Ouagari, et al. "Glycophorin A Protects K562 Cells from Natural Killer Cell Attack". The Journal of Biological Chemistry, vol. 270, No. 45, 1995, pp. 26970-26975.

Owens, et al. "Identification of two short internal ribosome entry sites selected from libraries of random oligonucleotides". PNAS, vol. 98, No. 4, 2001, pp. 1471-1476.

Paddison, et al. "Short hairpin RNAs (shRNAs) induce sequence-specific silencing in mammalian cells". Genes & Development, vol. 16, 2002, pp. 948-958.

Sivanandham, et al. "Cancer Vaccines: Clinical Applications". Principles and Practice of the Biologic Therapy of Cancer, Third Edition, S. Rosenberg, 2000, pp. 632-647, Lippincott Williams & Wilkins, Philadelphia, PA.

Verma, et al. "Gene therapy—promises, problems and prospects". Nature, vol. 389, 1997, pp. 239-242.

Agrawal, et al. "Cancer-associated MUC1 mucin inhibits human T-cell proliferation, which is reversible by IL-2.", *Natl. Med.*, 4(1):43-9 (1998).

Dall'Olio, et al., "Expression of beta-galactoside alpha 2,6-sialyltransferase does not alter the susceptibility of human colon cancer cells to NK-mediated cell lysis." *Glycobiology*. 7:507-513 (1997).

Natali, et al., *Heterogeneity in the expression of HLA and tumor-associated antigens by surgically removed and cultured breast carcinoma cells.* Cancer Res 1983; 43:660-666.

Pahlsson, et al., "Biochemical characterization of the O-glycans on recombinant glycophorin as expressed in Chinese hamster ovary cells." *Clycoconj. J.*, 11:43-50 (1994).

Peters, et al., "Preparation of immuno-therapeutic autologous tumour cell vaccines from solid tumours." *Cancer Res.*, 39:1353-1360 (1979).

Springer, et al., "Immunoreactive T and Tn epitopes in cancer diagnosis, prognosis, and immunotherapy." *J. Mol. Med.*, 75:594-602 (1997).

Van Rinsum, et al., "Specific inhibition of human natural killer cell-mediated cytotoxicity by sialic acid and sialo-oligosaccharides." *Int. J. Cancer*, 38:915-922 (1986).

Voshol, et al., "Cell surface glycoconjugates as possible target structures for human natural killer cells: evidence against the involvement of glycolipids and N-linked carbohydrate chains." *Glycobiology*, 3:69-76 (1993).

Wang, et al., "Second-generation adenovirus vectors." *Nat. Med.*, 2:714-716 (1996).

Werkmeister, et al., "Modulation of K562 cells with sodium butyrate. Association of impaired NK susceptibility with sialic acid and analysis of other parameters." *Int. J. Cancer*, 32:71-78 (1983).

Yu, et al., "RNA interference by expression of short-interfering RNAs and hairpin RNAs in mammalian cells." *Proc. Natl. Acad. Sci.*, 99:6047-6052 (1999).

Zhang, et al., "A MUC1 mucin secreted from a colon carcinoma cell line inhibits target cell lysis by natural killer cells." *Cellular Immunology*, 176:156-165 (1997).

Albert, "Dendritic cells acquire antigen from apoptotic cells and induce class I-restricted CTLs," *Nature*, 392:86-89 (1998).

Allison A. et al., "The role of cytokines in the action of immunological adjuvants," *Vaccine Design The Role of Cytokine Networks*, Gregoriadis ed., NATO ASI Series A: Life Science, vol. 293, pp. 1-9, Plenum Press, NY (1997).

Berd, "Autologous hapten-modified melanoma vaccine as postsurgical adjuvant treatment after resection of nodal metastases," *J. Clin. Oncol.*, 15:2359-2370 (1997).

Berthier-Vergnes, "Induction of IgG Antibodies Directed to a $M_r$ 31,000 Melanoma Antigen in Patients Immunized with Vaccinia Virus Melanoma Oncolysates," *Cancer Res.* 54:2433-2439 (1994).

Binder, "Cutting Edge: Heat Shock Protein gp96 Induces Maturation and Migration of CD11c$^+$Cells In Vivo," *J. Immunol.*; 165:6029-6035 (2000).

Bomford et al., "The control of the antibody isotype responses to recombinant human immunodeficiency virus gp120 antigen by adjuvants," *AIDS Res. Hum. Retroviruses*, 8:1765 et seq. (1992).

Bourdon, "Inhibition of Tumoral Graft Growth by Pretreatment with Normal or Heat-modified Tumoral Cells," *Ann. Immunology* 1, 43-63 (1981).

Cavaliere, "Selective heat sensitivity of cancer cells. Biochemical and clinical studies," *Cancer* 20:1351-1381 (1967).

Check, "Protection against transplanted and spontaneous lymphoma by inoculation of heat-altered syngeneic tumor cells in splenectomized mice," *Cancer*, 34:197-203 (1974).

Chen Z. et al., "Efficient Antitumor Immunity Derived From Muturation of Dendritic Cells That had Phagocytosed Apoptotic/Necrotic Tumor Cells," *International Journal of Cancer*, vol. 93, No. 4, pp. 539-548 (2001).

Clayman (ed.), The American Medical Association Encyclopedia of Medicine at 573-574, 576 and 1034 (1989).

Cox et al., "Adjuvants—A classification and review of their modes of action," *Vaccine*, vol. 15, pp. 248 et seq., (1997).

Cox et al., "Development of an Influenza-ISCOM.TM. Vaccine," in *Vaccine Design* at pp. 33-49 (1997).

Cryz, Jr., S.J., *Immunotherapy and Vaccines*, edited by Stanley J. Cryz, pp. 3-11, VCH, Weinheim, Germany (1991).

Dickson, "Hyperthermia in the treatment of cancer," *Lancet*, 1:202-205 (1979).

*Dictionary of Immunology*, pp. 3, 7, 46, 87-88, 94, 97, 105, 116.

Dressel, "Heat Shock Protein 70 Is Able to Prevent Heat Shock-Induced Resistance of Target Cells to CTL," *J. Immunol.*, 164:2362-2371 (2000).

Feng, "Stressed apoptotic tumor cells express heat shock proteins and elicit tumor-specific immunity," *Blood*, 97:3505-3512 (2001).

Ferencik, M., *Handbook of Immunochemistry*, p. 115-116, Chapman & Hall (1993).

Fujiwara, "Establishment of a tumor-specific immunotherapy model utilizing TNP-reactive helper T cell activity and its application to the autochthonous tumor system," *J. Immunol.*, 133:509-514 (1984).

Galluci, "Danger signals: SOS to the immune system," *Curr. Opin. Immunol.*, 13:114-119 (2001).

Galluci, "Natural adjuvants: Endogenous activators of dendritic cells," *Nat. Med.*, 11:1249-1255 (1991).

Goletz, et al., "Thomsen-Friedenreich Antigen: the "hidden" tumor antigen." Adv. Exp. Med. Biol., 535:147-62 (2003).

Giovanella, "Effects of Elevated Temperatures and Drugs on the Viability of L1210 Leukemia Cells," *Cancer Res.*, 30:1623-1631 (1970).

Gough M.J. et al., "Macrophages Orchestrate the Immune Response to Tumor Cell Death," *Cancer Research* 61, pp. 7240-7247 (2001).

Kotera Y. et al., "Comparative Analysis of Necrotic and Apoptotic Tumor Cells as a Source of Antigen(s) in Dendritic Cell-Based Immunization," *Cancer Research*, vol. 61, No. 22, pp. 8105-8109 (2001).

Luftig, R.B., *Microbiology and Immunology*, pp. 228-229, Lippincott-Raven Pub, Phila. (1998).
Mach, "Cytokine-secreting tumor cell vaccines," *Curr. Opin. Immunol.* 12, 571-575 (2000).
Melcher, "Apoptosis or necrosis for tumor immunotherapy: what's in a name?" *J. Mol. Med*, 77:824-833 (1999).
Melcher, "Tumor immunogenicity is determined by the mechanism of cell death via induction of heat shock protein expression," *Nat. Med.*, 4:581-587 (1998).
Mise, "Effect of Heat Treatment on Tumor Cells and Antitumor Effector Cells," *Cancer Res.*, 50:6199-6202 (1990).
Mitchell, "Active Specific Immunotherapy for Melanoma: Phase I Trial of Allogeneic Lysates and a Novel Adjuvant," *Cancer Res.*, 48:5883-5893 (1988).
Mondovi, "Increased immunogenicity of Ehrlich ascites cells after heat treatment," *Cancer*, (30)4:885-888 (1972).
Phillips, T., *Analytical Techniques in Immunochemistry*, pp. 307-310, Marcel Dekker, NY (1992).
Price, "Effect of heat and glutaraldehyde upon the immunogenicity of Meth A sarcoma cells," *Br. J. Cancer* 40:663-665 (1979).
Restifo, "Building better vaccines: how apoptotic cell death can induce inflammation and activate innate and adaptive immunity," *Curr. Opin. Immunol.*, 12:597-603 (2000).
Romani et al., "Proliferating dendritic cell progenitors in human blood," *J. Exp. Med.*, 180:83-93 (1994).
Sauter Birthe et al., "Consequences of Cell Death: Exposure to Necrotic Tumor Cells, but Not Primary Tissue Cells or Apoptotic Cells, Induces the Maturation of Immunostimulatory Dendritic Cells," *Journal of Experimental Medicine*, vol. 191, No. 3, pp. 423-433 (2000).
Schild, "gp96—the immune system's Swiss army knife," *Nat. Immunol.* 1:100-101 (2000).
Selawry, "Hyperthermia in Tissue-cultured Cells of Malignant Origin," *Cancer Res.*, 17:785-791 (1957).
Sensi, "Clonal Expansion of Lymphocytes in Human Metastases after Treatment With a Hapten-modified Autologous Tumor Vaccine,"*Clin. Invest.* 99:710-717 (1997).
Shaif-Muthana, "Dead or Alive: Immunogenicity of Human Melanoma Cells When Presented by Dendritic Cells," *Cancer Res.*, 60:6441-6447 (2000).
Somersan S. et al., "Primary Tumor Tissue Lysates Are Enriched in Heat Shock Proteins and Induce the Maturation of Human Dendritic Cells," *Journal of Immunology*, vol. 167, No. 9, pp. 4844-4852 (2001).
Todryk, "Heat shock protein 70 induced during tumor cell killing induces Th1 cytokines and targets immature dendritic cell precursors to enhance antigen uptake," *The Journal of Immunology*, 163:1398-1408 (1999).
Vermes, "A novel assay for apoptosis. Flow cytometric detection of phosphatidylserine expression on early apoptotic cells using fluorescein labelled Annexin V," *J. Immunol. Meth.*, 184:39-51 (1993).
Wells, "Heat shock proteins, tumor immunogenicity and antigen presentation: an integrated view," *Immunol. Today*, 21:129-132 (2000).
Zhang, "Selection of Tumor Antigens as Targets for Immune Attack Using Immunohistochemistry: II. Blood Group-Related Antigens," *Int. J. Cancer*, 73, 50-56 (1997).
PCT International Search Report for PCT/EP2004/009281.
U.S. Appl. No. 10/524,738, Amendment filed on Apr. 1, 2009.
Paul, W. E. (Ed.), *Fundamental Immunology*, p. 1007-1009, Raven Press, NY (1989).
Leffell, Mary S., "An Overview of the Immune System: The Molecular Basis for Immune Responses", *Human Immunology Handbook*, 1:1-45 (1997).
Snippe et al., "Adjuvant Directed Immune Specificity at the Epitope Level. Implications for Vaccine Development. A Model Study Using Semliki Forest Virus Infection of Mice," *Vaccine Design: The Role of Cytokine Networks*. pp. 155-166 (1997).
Anderson, "Human Gene Therapy," *Science*, 256:808-813 (1992).
Brummelkamp, et al., "A System for Stable Expression of Short Interfering RNAs in Mammilian Cells," *Science*, 296:550-553 (2002).
Elbashir, et al., "Duplexes of 21-nucleotide RNAs Mediate RNA Interference in Cultured Mammalian Cells," *Nature*, 411:494-498 (2001).
Isner, et al., "Clinical Evidence of Angiogenesis After Arterial Gene Transfer of phVEGF165 in Patient with Ischaemic Limb," *The Lancet*, 348:370-374 (1996).
Novina, et al., "siRNA-directed Inhibition of HIV-1 Infection," *Nature Medicine*, 8(7):681-686 (2002).
Ohyama, et al., "Dual Roles of Sialyl Lewis X Oligosaccharides in Tumor Metastasis and Rejection by Natural Killer Cells," *The EMBO Journal*, 18(6):1516-1525 (1999).
Ohyama, et al., "Natural Killer Cells Attack Tumor Cells Expressing High Levels of Sialyl Lewis X Oligosaccharides," *PNAS*, 99(21):13789-13794 (2002).
Ouagari, et al., "Glycophorin A Protects K562 Cells from Natural Killer Cell Attack," *The Journal of Biological Chemistry*, 270(45):26970-26975 (1995).
Owens, et al., "Identification of Two Short Internal Ribosome Entry Sites Selected from Libraries of Random Oligonucleotides," *PNAS*, 98(4):1471-1476 (2001).
Paddison, et al., "Short Hairpin Rnas (shRNAs) Induce Sequence-Specific Silencing in Mammalian Cells," *Genes & Development*, 16:948-958 (2002).
Sivanandham, et al., "Cancer Vaccines: Clinical Applications," *Principles and Practice of the Biologic Therapy of Cancer*, Third Ed., S. Rosenberg, pp. 632-647, Lippincott Williams & Wilkins, Philadelphia, PA (2002).
Verma, et al., "Gene Therapy—Promises, Problems and Prospects," *Nature*, 389:239-242 (1997).
Mivechi, "Heat Sensitivity, Thermotolerance, and Profile of Heat Shock Protein Synthesis of Human Myelogenous Leukemias," *Cancer Research*, 49:1954-1958 (1989).
Lozzio and Lozzio, "Human Chronic Myelogenous Leukemia Cell-Line with Positive Philadelphia Chromosome," *Blood*, 45(3):321-334 (1975).
Yoshima, et al., "Heat Shock Factor 1 Mediates Hemin-Induced *hsp70* Gene Transcription in K562 Erythroleukemia Cells," *JBC*, 273(39):25466-25471 (1998).
Samali, et al., "Thermotolerance and Cell Death are Distinct Cellular Responses to Stress: Dependence on Heat Shock Proteins," *FEBS Letters*, 461(3):306-310 (1999).
Huang, et al., "Heat-Induced Gene Expression as a Novel Targeted Cancer Gene Therapy Strategy," *Cancer Research*, 60:3435-3439 (2000).
Office Action, U.S. Appl. No. 10/524,738, date of mailing Oct. 5, 2006.
Office Action, U.S. Appl. No. 10/524,738, date of mailing Dec. 14, 2006.
Office Action, U.S. Appl. No. 10/524,738, date of mailing Aug. 10, 2007.
Office Action, U.S. Appl. No. 10/524,738, date of mailing Feb. 6, 2008.
Office Action, U.S. Appl. No. 10/524,738, date of mailing Aug. 4, 2008.
Advisory Action, U.S. Appl. No. 10/524,738, date of mailing Jan. 29, 2009.
Notice of Allowance, U.S. Appl. No. 10/524,738, date of mailing May 19, 2009.
Issue Notification, U.S. Appl. No. 10/524,738, date of mailing Sep. 19, 2009.
Cao, Y., et al., "Expression of CD175 (Tn), CD175s (sialosyl-Tn) and CD176 (Thomsen-Friedenreich antigen) on malignant human hematopoietic cells," *Int. J. Cancer*, 123:89-99 (2008).
Preliminary Amendment, U.S. Appl. No. 10/524,738, filed Feb. 16, 2005.
Reply to Restriction Requirement, U.S. Appl. No. 10/524,738, filed Nov. 6, 2006.
Reply to Office Action, U.S. Appl. No. 10/524,738, filed Jun. 14, 2007.
Reply to Office Action, U.S. Appl. No. 10/524,738, filed Dec. 10, 2007.
Reply to Office Action, U.S. Appl. No. 10/524,738, filed May 6, 2008.
Reply to Final Office Action, U.S. Appl. No. 10/524,738, filed Jan. 2, 2009.
Amendment and Request for Continued Examination, U.S. Appl. No. 10/524,738, filed Apr. 1, 2009.

\* cited by examiner

| NM-F9 | K562 cells before magnetic separation | |
|---|---|---|
|  |  | TF |
|  |  | Tn |
|  |  | GPA |
|  |  | AGPA |
|  |  | MUC1 |

A

B

BSA  GPA  NM-F9  LMW  AGPA

TF

BSA  GPA  AGPA  NM-F9  LMW

KDa
110
90   AGPA
51
36
29
21

TUMOUR CELL LINES AND USES THEREOF

The present invention relates to a cell line selected from the group consisting of (a) a cell line denominated NM-F9 having the DSMZ accession number DSM ACC2606; (b) a cell line denominated NM-D4 having the DSMZ accession number DSM ACC2605; and subclones of (a) or (b). Additionally, the present invention provides a lysate of the cell lines or a molecule or mixture of molecules obtained from these cell lines as well as dendritic cells loaded with said lysate, co-cultivated or fused with cells from the cell lines, or a molecule or mixture of molecules obtained from these cell lines of the present invention. Moreover compositions, preferably pharmaceutical or vaccine compositions are provided which comprise the cell lines, lysate, molecules, mixture of molecules or dendritic cells of the present invention. In another aspect the present invention relates to methods for producing the aforementioned compositions. Furthermore, methods and uses for vaccination against or treatment or prevention of cancers and/or tumourous diseases are provided.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The concept of host immunity against tumour was developed by Ehrlich (Ehrlich P. Uber den jetzigen Stand der Karzinom-forschung. In: Himmelweit F., ed. The collected papers of Paul Ehrlich—Vol. II Immunology and cancer research. London: Pergamon Press, 1957:559) about a century ago and was later reinforced in the early 1900s by several laboratories that studied transplantable tumour cell lines in mice. In 1910, Contamin (Cantamin M A. Immunization contre le cancer de la souris inoculec avec des tumours modifes par les rayons. Academie Des Sciences 1910; 150:128) demonstrated the development of protective immunity against, transplantable tumour cells in mice immunized with the same irradiated tumour cells. In 1935 Besredtka and Gross (Besredka A, Gross L. Durole dela peau dans la sarcomatose de la souris. Ann Inst Pasteur 1935; 55:402-416) showed that some animals inoculated with tumour cell homogenate experienced tumour regression, as well as protection to tumour reinoculation challenges. Since these early times anti-tumour vaccination saw encouraging results as well as disappointing drawbacks. Recently, the theory of immunosurveillance against cancer cells faced a revival. The heterogeneity in the expression of tumour associated antigens (TAA) has been documented throughout the various tumours (Natalie P G, Giacomini P, Bigotti A, et al. Heterogeneity in the expression of HLA and tumour-associated antigens by surgically removed and cultured breast carcinoma cell. Cancer Res 1983; 43:660-666; Houghton A N, Davis L J, Phenotypic heterogeneity of melanoma. In: Bagnara J T, ed. Advances in pigment cell research, New York: Alan R. Liss Inc. 1988:333-342) and clearly plays a role in the escape of tumour cells from immunosurveillance (Jager E., Ringhoffer M, Altmannsberger M, et al. Immunoselection in vivo:independent loss of MHC class I and melanocyte differentiation antigen expression in metastatic melanoma. Int J Cancer 1997; 71:142-147). Therefore, the development of tumour cell lysate vaccines (TCLV's) and whole cell vaccines (WCVs) were approached in order to generate polyvalent vaccines. Nowadays two or more cell lines of the same histiotype are used for the development of cancer vaccines in order to offset any potentially lost antigens. These are used to tackle tumours of the same tissue type or of different tissue type. Autologous or allogeneic tumour cells are the major components of TCLVs or WCVs.

The major drawback of these approaches is that a mixture of various cell lines has to be used which makes the generation of these vaccines laborious and expensive. A further disadvantage is that carcinoma cells are, in a biotechnological sense, not suitable because of their growth and proliferation characteristics and requirements. In particular, the growth and proliferation requirements for such carcinoma cells are usually very specific and need to be carefully established and maintained which leads to a laborious and cost intensive production process. Another problem with carcinoma cells used for the production of TCLVs and WCVs is that they often have an endogenous virus load, i.e. such cells may harbour viruses (e.g. retroviruses) which poses problems in the production of autologous or allogeneic vaccines and, more importantly when using virus containing cells (or lysates thereof) for vaccination purposes. Additionally, carcinoma cells used so far for the production of TCLV or WCV grow with a comparingly very slow doubling rate and/or grow as adherent culture which does not allow growth in high cell densities as well as easy harvesting. A large amount of the same batch of cells is, however, desired to produce, in order to make sure that the obtained TCLVs and WCVs have a continuous and high quality standard.

Beside the technical problems with cells used so far for the production of TCLVs and WCVs, there are also major drawbacks with the immunogenicity of said cells. This is because said cells often harbour only very specific antigens of specific tumours. Thus, the generation of a pan-carcinomic multivalent TCLVs or WCVs which are suitable for various carcinomas with several shared tumour antigens is an unpredictable and difficult task. Additionally, it is also known that most of the highly specific tumour antigens which are expressed on the surface of tumour cells and against which it is highly desirable to obtain an immune response during immunization are carbohydrate antigens. Due to the complex nature of the glycosylation machinery, especially in mammalian cells where more than 200 enzymes are involved in the glycosylation of membrane molecules, the generation of cell lines which stably express high amounts of desired carbohydrate tumour antigens is very difficult and can not be predicted because of the complex interplay of this large amount of different factors which is largely unknown and it can be expected that they have in addition feed-back loops and complex substrate requirements depending on the complex interplay. This holds especially true when several carbohydrate tumour antigens want to be combined on a single cell as it is the case for a pan-carcinomic polyvalent WCV or TCLV vaccine. In contrast, modification of a cell with protein antigens is a straight forward technology known to those skilled in the art. The outstanding membrane tumour antigen in specificity is the so-called Thomsen-Friedenreich antigen (TF), a carbohydrate disaccharidic structure which virtually only occurs on tumour cells and nearly all carcinoma types (Goletz S., Cao Y, Danielczyk A., Ravn P., Schöber U., and Karsten U. Thomsen-Friedenreich antigen: the "hidden" tumour antigen. Adv. Exp. Med. Biol. 2003; 535:147-62) 2003). Thereby it is the membrane bound tumour antigen with the highest or at least amongst those with the highest tumour specificity. Another carbohydrate tumour antigen with very high tumour specificity is Tn, a TF related antigen. Another pan-carcinomic tumour epitope is a special novel epitope of MUC1 (polymorphic epithelial mucin), which we will call TA-MUC1 herein, and which is a conformational epitope in which particular glycosylations at the PDTRP region induce a conformation which is tumour specific as for example described in PCT/EP03/08014. In addition MUC1 in itself is a well known pan-carcinomic tumour marker with peptide epitopes. The expression of said carbohydrate or carbohydrate related antigens, however, is often not stable when tumour cells of patients are cultured. In addition higher amounts of the antigens are preferred in order to increase the immune responses which renders the generation even more problematic. In conclusion there are problems or drawbacks associated with the cells used for the production of TCLVs or WCVs.

Thus, there is a need in the art for multivalent tumour cell vaccines which can be easily produced in large amounts and in a highly reproducible manner and which also stably express the highly specific tumour antigens shared by many carcinomas (pan-carcinomic antigens).

The solution to this technical problem underlying the present invention is achieved by providing the embodiments characterized in the claims.

Accordingly, the present invention relates to a cell line which expresses TF on the cell surface and that expresses MUC1, preferably TA-MUC1 on the cell surface and that express glycophorin, preferably as asialoglycophorin on the cell surface. Preferably, the present invention relates to a cell line selected from the group consisting of (a) a cell line denominated NM-F9 having the DSMZ accession number DSM ACC2606; (b) a cell line denominated NM-D4 having the DSMZ accession number DSM ACC2605; and (c) subclones of (a) or (b).

Said cell line which expresses TF on the cell surface and that expresses MUC1, preferably TA-MUC1 on the cell surface and that express glycophorin, preferably as asialoglycophorin on the cell surface, can be generated from any cell line which expresses endogenously or recombinantly MUC1 and glycophorin, preferably K562 cells. In detail the procedure is described for K562 cells in the examples 2 and 3. Briefly, the cells are analysed for TF expression by any method available to skilled persons, preferably by flow cytometry (described in example 2A4) or immunocytochemistry (described in example 3A-1). TF-positive cells are selected by using the monoclonal antibodies A78-G/A7 or PankoMab as described in example 2A-2. In case, the number of TF-positive cells is to low, the TF-negative cell line is treated with a mutagen, preferably a chemical mutagen, preferably ethyl methanesulfonate (EMS) as described in example 2A-1. Thereafter, the TF-positive cells are selected as described above. The selection for TF-positive cells need to be repeated and thereafter TF-positive cells need to be cloned to receive cells that stably TF-positive as described in example 2A-2.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

Surprisingly, it was possible to generate cell lines (such as the deposited NM-F9 and NM-D4) from K562 cells (ATCC CCL-243) that express several highly specific tumour associated carbohydrate antigens, namely the TF in very high amounts, and asialoglycophorin (AGPA) consisting of the carrier protein glycophorin and TF groups in high amounts, and LeX in high amounts, and TA-MUC1 in moderate amounts, and Tn in comparably low amounts. Additionally, it was surprising that said cell lines are highly immunostimulatory and are able to activate immune responses against said tumour antigens.

The generation of exposed and stably expressed TF groups in suitable densities on the cells of the cell lines of the present invention is an unpredicted finding, since TF is a core sugar in O-glycosylation which is normally cryptically hidden in longer carbohydrate chains which are build up via a complex pattern of glycosyltransferases. Due to the complex O-glycosylation machinery in which large amounts of different enzymes are involved which are depending on each other and on complex substrate properties, prerequisites for an expression of the inner core sugar Core-1, which equals TF when exposed were very difficult. Moreover, the combined expression of high amounts of TF and glycophorin on the cells of the cell lines of the present invention is highly advantageous. TF is present on the glycophorin (GPA) which can hardly be increased by neuramidase treatment showing that GPA exists as asialoglycophorin (AGPA) on the membrane of NM-F9 and NM-D4. Glycophorin A is a marker for erythrocytes. Other cells normally lack glycophorin. The advantage of TF in form of AGPA is that it is known from studies from Springer (Springer G F; Immunoreactive T and Tn epitopes in cancer diagnosis, prognosis, and immunotherapy. J. Mol. Med. 1997; 75:594-602) that AGPA in a crude preparation obtained from a crude process from red blood cells in combination with enzymatic desialylation results in an effective cancer vaccination hardly or not met by other treatments. The present invention uses these large advantage of AGPA in form of a cell line that stably express AGPA. This has a lot of advantages compared with the conventional preparation of AGPA from blood cells. For example 1) there is no need of any enzymatic treatment for the production of AGPA since the cell lines presented in this invention synthesize the TF-positive AGPA in contrast to red blood cells which synthesize the TF-negative GPA. 2) It does not need preparation from blood samples which can be contaminated with viruses and prions and which are heterogeneous in composition, highly variable from batch to batch and a difficult purification process based on phenol extraction. 3) These advantages are combined with other potent antigens, e.g. Tn, TA-MUC1, MUC1 and LeX. The TF groups on the glycophorin backbone molecules in form of AGPA are in itself highly immunogenic when purified which is also shown by these historical studies. The cell line K562 (i.e. the origin of the cell lines of the present invention) is known to express glycophorin but not TF. Accordingly, it is assumed that the cell lines of the present invention contain a genetic defect (for example a defect in specific glycosyltransferases) which leads to an expression of TF, which is normally not present on K562 cells. It is now possible to provide a cell line which expresses besides glycophorin also the TF-antigen without the need for any further modification. In addition, NM-D4 was identified to be particularly suitable for generation MUC1 with the tumour specific conformational epitope TA-MUC1, the tumour epitope of MUC1 which is apparently a conformational epitope induced by particular glycosylation modifications in the immunodominant region of MUC1 comprising the peptide sequence PDTRP. NM-F9 and NM-D4 express TA-MUC1 in an amount of about $1-1.5*10^5$ binding sites for TA-specific antibodies which is not a low amount and which was until now not known. In contrast, it was shown that MUC1 in general is expressed in K562 in a hardly or not detectable amount (Zhang K, Sikut R, Hansson G C. A MUC1 mucin secreted from a colon carcinoma cell line inhibits target cell lysis by natural killer cells. Cellular Immunology, 1997; 176: 158-165) and hence it was not expected to discover suitable amounts of MUC1 and TA-MUC1 on these cells or cells derived from K562. Furthermore, MUC1 is known to be immunosuppressive by inhibiting proliferation of T cells (Agrawal B, Krantz M J, Reddish M A, Longenecker B M. Cancer-associated MUC1 mucin inhibits human T-cell proliferation, which is reversible by IL-2.: Nat. Med. 1998 January; 4(1):43-9) and killing of NK cells (Zhang K, Sikut R, Hansson G C. A MUC1 mucin secreted from a colon carcinoma cell line inhibits target cell lysis by natural killer cells. Cellular Immunology, 1997; 176:158-165). However, MUC1 expressed on NM-F9 or NM-D4 cells was not immunoinhibitory (see the results of the appended examples; in particular the in vivo data). Furthermore, NM-F9 or NM-D4 cells were found to express the carbohydrate tumour antigens Tn but in low amounts and high amounts of LeX (equals Lewis X or Le$^x$) which are other carbohydrate antigens expressed on carcinoma cells. Thus, the accumulation of various pan-carcinomic antigens, including TF, in high suitable' densities combined with the biotechnologically advantageous capabilities of K562 (in particular to be a well-established and biotechnolgically suitable cell line) renders the NM-F9 and/or NM-D4 cell line of the present invention a suitable master cell line which can be used for all or many different tumour and carcinoma types with according relevant antigens, in particular TF (including TF in a particular immunogenic form on the carrier GPA as AGPA), TA-MUC1, MUC1, Tn and/or LeX as well as other tumour antigens which are naturally part of NM-D4, NM-F9 mainly originating from the K562 phenotype, and which were not further investigated herein, for example BCR-ABL fusion gene. According to the present invention the term "cell line" means a cell line or cells which can be grown under in vitro culture conditions as indicated, e.g., in the appended examples. Additionally, said term also embraces cells of a single type that have been grown in the laboratory for several generations. The term "cell lines of the present invention" relates to (a) cell line(s) that express TF on the cell surface and that express MUC1, preferably TA-MUC1 on the cell surface and that express glycophorin, preferably as asialoglycophorin on the cell surface. Moreover, said term relates preferably to the specific cell-clones NM-F9 and/or NM-D4 as well as subclones thereof. The meaning of "subclones" is described herein elsewhere. The term "NM-F9" as used herein, is equivalent to terms like e.g. "F9"; "clone F9" or "K562-F9" and relates to cells of a cell line or a cell line deposited with the Deutsche Sammlung für Mikroorganismen und Zellkulturen GmbH ("DSMZ") on Aug. 14, 2003 and having the deposit number DSM ACC2606.

The term "NM-D4" as used herein, is equivalent to terms like e.g. "D4"; "clone D4" or "K562-D4" and relates to cells of a cell line or a cell line deposited with the Deutsche Sammlung für Mikroorganismen und Zellkulturen GmbH ("DSMZ") Aug. 14, 2003 and having the deposit number DSM ACC2605.

The DSMZ is located at the Mascheroder Weg 1b, D-38124 Braunschweig, Germany. The aforementioned DSMZ deposits were made pursuant to the terms of the Budapest treaty on the international recognition of the deposit of microorganisms for purposes of patent procedure. The NM-F9 and NM-D4 cell lines have been deposited by Nemod Biotherapeutics GmbH & Co. KG, Robert-Rossle-Strasse 10, 13125 Berlin, Germany (i.e. the depositor) who authorise the applicant of the present application to refer to the deposited biological material described herein and give their unreserved and irrevocable consent to the applicant of the present application that the deposited biological material described herein be made available to the public in accordance with Rule 28(1)(d) of the European Patent Convention.

The term "subclones" when used in accordance with the present invention means cells or cells of a cell line which are derived from NM-F9 or NM-D4 and which occur due to naturally occurring alterations, e.g., mutations, but having similar characteristics as the above-mentioned cell lines. In particular, the subclones as mentioned herein have at least the following similar characteristics (a) to (c) which they share with NM-D4 and NM-F9:

(a) they express TF on the cell surface;
(b) they express MUC1 and preferably TA-MUC1 on the cell surface; and
(c) they express glycophorin, preferably as asialoglycophorin on the cell surface.

The term "TA-MUC1" as used herein, is a conformational epitope in which particular glycosylations at the PDTRP region induce a conformation which is tumour specific. Said TA-MUC1 has been described in great detail for example in PCT/EP03/08014. It is preferred that the aforementioned antigens are detectable (e.g. in FACS; ELISA or the like) with the following antibodies: A78-G/A7, Nemod-TF1 and/or Nemod-TF2 (Goletz S., Cao Y, Danielczyk A., Ravn P., Schöber U., and Karsten U. Thomsen-Friedenreich antigen: the "hidden" tumour antigen. Adv. Exp. Med. Biol. 2003; 535:147-62, all obtainable from NEMOD Immuntherapie AG (which is now NEMOD Biotherapeutics GmbH & Co. KG, Berlin, for TF; A76-A/C7, VU-11E2, VU-11D1, BC4E549, VU-12E1, VU-3D1 and b-12 for MUC1 and preferably A76-A/C7 and more preferably PankoMab for TA-MUC1). In addition, the aforementioned antibodies are known in the art. Antibody A76-A/C7 is can be obtained from NEMOD Biotherapeutics GmbH & Co. KG. The PankoMab antibody is described in Christensen A P, Danielczyk A, Stahn R, Goletz S. Simple separation of DNA in antibody purification. Protein Expr Purif, in press, and preferably A83-C/B12 for glycophorin and preferably A63-C/A9 for asioaloglycophorin). Further, it is preferred that the subclones of the present invention (d) grow in suspension under the standard laboratory conditions (e.g. as detailed by the DSMZ for K562).

Methods for determining the presence of the aforementioned carbohydrate-antigens on the surface of cell lines (e.g. the cell lines of the present invention) are well-known to the skilled person and include for example ELISA; FACS; Blotting-techniques like Western-Blot and/or glycosylation analysis techniques as described and provided for example by Oxford GlycoSystems or Glycotope GmbH. In addition, the appended examples describe the characterization of the carbohydrate surface antigens of the cell lines of the present invention in great detail.

Characterization of NM-F9 and NM-D4

Figure 2:
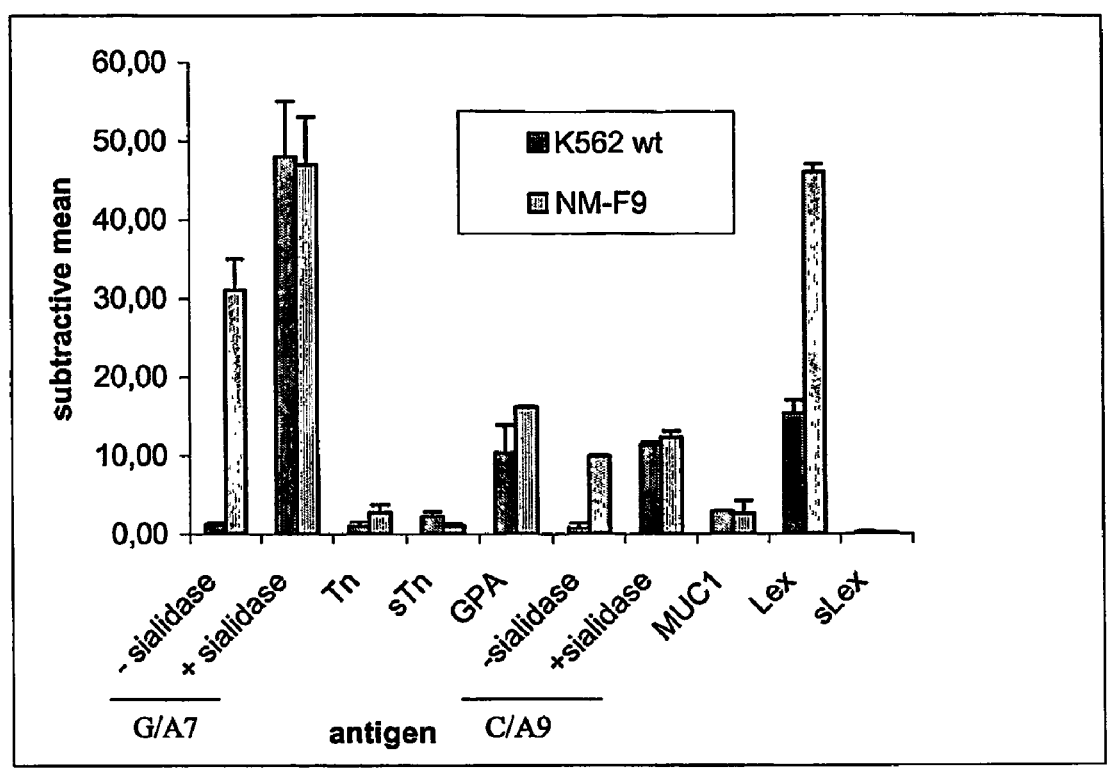

TF which is absent on K562 is strongly and stably expressed on NM-F9 and NM-D4 as shown by binding of the TF specific antibodies A78-G/A7 (FIG. 1), Nemod-TF1 and Nemod-TF2. Neuramidase treatment of strongly TF-positive NM-F9 reveals that sialylation is largely reduced but some TF is still sialylated (FIG. 2). The latter fact is depending on media conditions.

NM-F9: Beside the very strong expression of TF, Tn and Sialyl-Tn, which are both weakly expressed in K562 wt (K562 wild type; equals K562 as obtained from DSMZ), are up-regulated and down-regulated, respectively. (FIG. 1 and FIG. 2) To determine whether increased carrier protein expression was in part responsible for these changes in TF expression, the expression of glycophorin A (GPA) and MUC1, major known carriers for TF, were analysed. Clearly, no different expression level was seen for MUC1 and only a minor increase in GPA (FIG. 1E, F, I, J and FIG. 2). In contrast, the binding of the antibody A63-C/A9, which recognizes glycophorin A only if glycosylated with TF at a certain site therefore acting as a marker for asialoglycophorin A (AGPA), the TF glycosylated version of GPA, is very strong on NM-F9 and is not above background in K562 wt. These results indicate that the increased TF expression on NM-F9 is caused by a strongly reduced ability of the cell to sialylate which is supported by the binding studies with the lectins SNA, PNA and MAA (FIG. 3A) and the determination of the sialic acid content in the membrane fraction of K562 wt and NM-F9 cells (FIG. 3B). Lectin staining with MAA and SNA revealed that the total amount of $\alpha$2-3- and 2-6-linked sialic acids on membrane proteins and lipids was about five-fold and two-fold, respectively, lower in NM-F9 cells (FIG. 3A). Binding of the sialylation-sensitive lectin PNA which preferentially binds to TF but also other desialylated terminal galactose residues increased about 33-fold in NM-F9 (FIG. 3A). Finally, the chemically determined content of sialic acids in the cell membrane was almost three-fold reduced in NM-F9 (FIG. 3B).

Interestingly, $Le^x$, a complex carbohydrate tumour marker on N- and O-glycans, was present on K562-wt cells (i.e. K562 wildtype cells as for example provided by the DSMZ) but its synthesis was strongly induced in NM-F9 cells (FIG. 2). However, the sialylated form of $Le^x$ ($s\text{-}Le^x$), as well as other Lewis carbohydrate antigens (i.e. $Le^a$, $s\text{-}Le^a$, $Le^y$), were absent in K562-wt and NM-F9 cells. UEAI, which detects terminal fucose in various linkages including fucose on $Le^x$ and $sLe^x$, did only weakly bind to K562 wt but strongly to NM-F9. This assumes that the increased $Le^x$ is generated by an up-regulation of fucosylation which was not further investigated.

NM-D4: The clone NM-D4 has similar properties as NM-F9. They show a very similar expression of, for example TF and $Le^x$ (very strong), GPA (strong), and Sialyl-Tn and $s\text{-}Le^x$ (very low or lacking). Differences are seen in a strong increase in TA-MUC1 and some decrease in Tn and the A63-C/A9 epitope, whereby the latter is still strongly expressed on NM-D4. In order to see if the number of TA MUC1 epitopes on membrane bound MUC1 are increased, the number of binding sites of PankoMab on K562 wt, NM-F9 and NM-D4 and the affinity of the binding was determined by Scatchard analysis using radiolabelled $^{111}$In-PankoMab (table 1). Scatchard analysis allows the determination of the maximum number of antibody molecules bound per cell and the apparent association constant of the binding reaction. Plotting the ratio of specifically bound and free antibody against the concentration of specifically bound antibody reveals a straight line. The binding capacity per cell was calculated from the intercept value at the abscissa and the association constant from the slope of the line. Surprisingly, the number of binding sites of PankoMab was not elevated in NM-F9 or NM-D4. On the contrary, NM-D4 and NM-F9 have about 60-65% of the number of binding sites as K562 wt. However, the affinity of the interaction between PankoMab and the cells was changed. While PankoMab recognizes MUC1 on NM-F9 with only a slight increase in affinity, MUC1 on NM-D4 is recognized with a 5 times increased affinity compared to MUC1 on K562 wt. This reflects that the altered truncated glycosylation leads to a better accessibility and/or folding of the complex carbohydrate-induced conformational tumour epitope of MUC1 (TA-MUC1) which is more prevalent in NM-D4 than in NM-F9. These determinations also show that MUC1, including TA-MUC1 is present on NM-F9, NM-D4 and K562 wt with an amount of antibody binding sites between about $1\text{-}1.5*10^5$, which is not low and contradicts the non- or hardly detectable amounts of MUC1 on K562 wt reported earlier (Zhang K, Sikut R, Hansson G C. A MUC1 mucin secreted from a colon carcinoma cell line inhibits target cell lysis by natural killer cells. Cellular Immunology, 1997; 176:158-165).

The given numbers and fold changes of expression, mainly performed in FACS analyses, are not absolute for the description of NM-D4 and NM-F9 because of several reasons: Inherent in the technology of FACS are varieties in absolute intensities from measurement to measurement, setting of the gates also has an influence; Media conditions can influence the residual sialylation amount of NM-F9 and NM-D4; inherent for cell cultures is, even with stable expressing clones, a slight variation in the expression amounts which also might change during cell cycle.

In a further embodiment the cell lines of the present invention comprise a vector. Such a vector may be, e.g., a plasmid, cosmid, virus, phagemide, bacteriophage or another vector used e.g. conventionally in genetic engineering or in transfection of mammal cells and may comprise further genes such as marker genes which allow for the selection of said vector in a suitable host cell and under suitable conditions. Said vector may be one selected from commercially available vectors. Nonlimiting examples include plasmid vectors and expression systems compatible with mammalian cells, such as pcDNA vectors, pSec vectors, pCMV vectors, pCEP4 (all Invitrogen), pRK5, pMC1 neo (Stratagene), pSG5 (Stratagene), pBK vectors (Stratagene) EBO-pSV2neo, pBPV-1, pdBPVMMTneo, pRSVgpt, pRSVneo, pSV2-dhfr, pTRE vectors (Clontech), pet-On/Off vectors (Clontech), and bicistronic and bi-directional vectors (e.g. pIRES vectors, pBI Vectors, Clontech)). For vector modification techniques, see Sambrook and Russel "Molecular Cloning, A Laboratory Manual", Cold Spring Harbor Laboratory, N.Y. (2001). Vectors can contain one or more replication and inheritance systems for cloning or expression, one or more markers for selection in the host, e.g., antibiotic resistance, and one or more expression cassettes. For use in patients it is preferred to use selection systems and/or singly cell cloning without introduction of antibiotic resistance markers.

In a further embodiment, said vector comprises a nucleic acid molecule. The nucleic acid molecule according to the invention may be any type of nucleic acid, e.g. DNA or RNA. The DNA may, for example, be genomic DNA; synthetic DNA or cDNA. The RNA may be, e.g., mRNA. The nucleic acid molecule may be natural, synthetic or semisynthetic or it may be a derivative, such phosphorothioates. Furthermore, the nucleic acid molecule may be a recombinantly produced chimeric nucleic acid molecule comprising any of the aforementioned nucleic acid molecules either alone or in combination. The nucleic acid molecules comprised by said vector can be synthesized by standard methods, isolated from natural sources, or prepared as hybrids. Ligation of the coding sequences to transcriptional regulatory elements (e.g., promoters, enhancers, insulators or the like) and/or to other amino acid encoding sequences can be carried out using established methods. Said vector is introduced into the cells of the cell lines of the present invention by methods commonly known in the art, for example, lipofection, electroporation, Ca-Phosphate-' transfection and the like.

Furthermore, the vectors may comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression comprise for example the CMV-HSV thymidine kinase promoter, SV40, RSV-promoter (Rous sarcoma virus), human elongation factor 1α-promoter, CMV enhancer, CaM-kinase promoter or SV40-enhancer. For the expression in the cells/cell lines of the present invention, several regulatory sequences are well known in the art. For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3, pcDNA5 (Invitrogen). An expression vector according to this invention is at least capable of directing the replication, and preferably the expression, of nucleic acids contained therein. Suitable origins of replication include, for example, the SV40 viral and the origins of replication. Suitable termination sequences include, for example, the bovine growth hormone, SV40, lacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-animal cells. The vector may further comprise nucleic acid sequences encoding for secretion signals. Such sequences are well known to the person skilled in the art. Furthermore, depending on the expression system used, leader sequences capable of directing e.g. an expressed polypeptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the extracellular membrane. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow. Of course, the vector can also comprise regulatory regions from pathogenic organisms.

Furthermore, said vector may also be, besides an expression vector, a gene transfer and/or gene targeting vector. Gene therapy, which is based on introducing therapeutic genes (for example for vaccination) into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242 and references cited therein. The vectors as described herein above may be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for the nucleic acid molecule comprised by the vectors comprised by the cell lines of the present invention.

In another preferred embodiment of the present invention the nucleic acid molecule comprised by the aforementioned vector encodes a polypeptide or fragments of the polypeptide selected from the group consisting of a cytokine, like IL-2, IL-12, IL-15, antigen presenting molecules like MHC class I and MHC class II molecules, costimulatory molecules, like CD80 and CD86, growth factors like GM-CSF, T cell epitopes or multimers thereof, tumour antigens or fragments thereof, hormones or sexual hormones, like FSH, hCG, insulin, adjuvants or fragments of adjuvants, like pan T-cell helper epitopes, antibodies and other molecules, like erythropoietin, glycophorin or forms of antigens which are lacking transmembrane domains for secretion, like glycophorin with lacking transmembrane and intracellular part but with an additional secretion signal or any combination thereof.

The term "antibody" comprises derivatives or fragments thereof which still retain the binding specificity. Said term furthermore includes chimeric, single chain and humanized antibodies, as well as antibody fragments, like, inter alis, Fab fragments. Antibody fragments or derivatives further comprise F(ab')2, Fv or scFv fragments; see, for example, Harlow and Lane ("Antibodies, A Laboratory Manual", CSH Press, Cold Spring Harbor, 1988). It is in particular preferred that the antibodies/antibody constructs as well as antibody fragments or derivatives to be employed in accordance with this invention or capable to be expressed in a cell.

Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to recombinantly generated/synthesized antibodies. The term also relates to intact antibodies as well as to antibody fragments thereof, like, separated light and heavy chains, Fab, Fab/c, Fv, Fab', F(ab')2. The term "antibody molecule" also comprises bifunctional antibodies and antibody constructs, like single chain Fvs (scFv) or antibody-fusion proteins. It is also envisaged in context of this invention that the term "antibody" comprises antibody constructs which may be expressed in cells, e.g. antibody constructs which may be transfected and/or transduced via, inter alis, viruses or vectors.

It is also envisaged that the polypeptide encoded by the nucleic acid comprised by a vector which is comprised by the cell line of the present invention is glycosylated and/or pegylated.

Generation and production of molecules (as for example glycoproteins) with lacking or low sialylation which are modified for example by PEGylation or other suitable molecules and techniques are known to those skilled in the art in order to improve their biological activity, their detectability and/or pharmaceutical suitability. Thereby molecules as glycoproteins with no or low amount of sialic acids are generated by expressing these molecules in the cell lines of the present invention, in particular in the cell line NM-F9, NM-D4. These molecules are isolated either from the cells or preferentially from the media of the cell cultures of these cells by expression as secreted molecules by methods known to those skilled in the art. The molecules are further modified by chemical or enzymatic methods, for example by PEGylation, attachment of fluorochromes, chemical linkers, peptides, proteins or other chemical molecules like biotin, known to those skilled in the art.

One preferred form is the PEGylation using CMP-Sialic acid linked to PEG in combination with one or several sialyltransferases as for example known for GlycoPegylation™ described by Neose Inc. Molecules expressed by the cells of the invention have the advantages: either, to (i) allow a higher and/or more effective and/or more controllable PEGylation at the sugar chains because of the lack or low amounts of sialylated carbohydrate sites which results in biologically improved molecules in sense known to be associated with PEGylation and/or a more efficient and/or standardizable/controllable process; or (ii) to allow the attachment of the modification to glycan sites which are not possible to be attached conventially or only by means of complex additional modification prior to the addition of the modification; or (iii) to lack the requirements to partially or completely desialylate the target molecule in order to obtain a suitable PEGylation by the known processes. Molecules expressed by standard expression systems as for example CHO, NSO, Per.C6 or HEK-cells have a higher sialylation of the expressed molecules than those expressed by cells of the present invention. Therefore the conventionally expressed molecules either have a lower or less efficient modification or have to be enzymatically or chemically desialylated in vitro and further purified which is labour and cost intensive especially when produced for clinical use and often generate problems in imposing a standardized controllable process to the high clinical requirements. In contrast, the advantage of the present invention is that the use of the cell lines of the invention and the nucleic acid molecules expressed in these cell lines is that the steps connected with desialylation will be unnecessary and the modification process is more efficient, better standardizable and controllable, cheaper, and/or faster. In comparison to standard technologies this process is often advantageous since the PEGylation does not occur at the peptide backbone and hence often reduces the activity in vitro but is further away from the active sites avoiding a reduction of the in vitro bioactivity. Besides the PEGylation other chemical or enzymatic modifications are preferred in combination with molecules expressed in the cell lines of the invention: e.g. bioactive or functional compounds like carbohydrates, modified carbohydrates, peptides, linkers, water-soluble polymers, toxins, fluorochromes, binding molecules like antibodies or antibody fragments, chemokines or cytokines, hormones or growth factors, or other bioactive molecules are attached via the carbohydrate PEGylation (not restricted to the examples). The method of attachment is known to those skilled in the art. Preferably the attachments occur via a glycosyl-linkage group known to those skilled in the art. The advantage(s) of using molecules expressed by the cells of the present invention is (are) the same as those described above for the PEGylation. In addition, the in vitro modification by carbohydrate or modified carbohydrates using the molecules expressed by the cells of the present invention enables a controlled attachment and bias towards certain types of sialic acids, sialic acids linkages and positions of attachment which is beneficial for the biological activity of the molecule and allows a customisation of the sialic acid pattern.

Alternatively or additionally the cell lines of the present invention may comprise an anti-sense, iRNA, siRNA or ribozyme in order to silence unintended genes which are expressed or might be expressed in the cell lines of the present invention, e.g. when employing the cell lines of the present invention as vaccines. An siRNA approach is, for example, dislosed in Elbashir ((2001), Nature 411, 494-498)). It is also envisaged in accordance with this invention that for example short hairpin RNAs (shRNAs) are employed. The shRNA approach for gene silencing is well known in the art and may comprise the use of st (small temporal) RNAs; see, inter alia, Paddison (2002) Genes Dev. 16, 948-958. Approaches for gene silencing are known in the art and comprise "RNA"-approaches like RNAi or siRNA. Successful use of such approaches has been shown in Paddison (2002) loc. cit., Elbashir (2002) Methods 26, 199-213; Novina (2002) Mat. Med. Jun. 3, 2002; Donze (2002) Nucl. Acids Res. 30, e46; Paul (2002) Nat. Biotech 20, 505-508; Lee (2002) Nat. Biotech. 20, 500-505; Miyagashi (2002) Nat. Biotech. 20, 497-500; Yu (2002) PNAS 99, 6047-6052 or Brummelkamp (2002), Science 296, 550-553. These approaches may be vector-based, e.g. the pSUPER vector, or RNA pollll vectors may be employed as illustrated, inter alia, in Yu (2002) loc. cit.; Miyagishi (2002) loc. cit. or Brummelkamp (2002) loc. cit. "Anti-sense" and "antisense nucleotides" means DNA or RNA constructs which block the expression of the naturally occurring gene product. As used herein, the terms "antisense oligonucleotide" and "antisense oligomer" are used interchangeably and refer to a sequence of nucleotide bases that allows the antisense oligomer to hybridize to a target sequence in an RNA by Watson Crick base pairing, to form an RNA: oligomer heteroduplex within the target sequence.

It is also envisaged that the cells of the cell lines of the present invention are genetically engineered, mutated or infected by oncogenic viruses or via random mutagenesis using chemicals, like EMS (ethyl methanesulfonate). In the context of the present invention the term "genetically engineered" is used in its broadest sense for methods known to the person skilled in the art to modify desired nucleic acids in vitro and in vivo such that genetic modifications are affected and genes are altered by recombinant DNA technology. Accordingly, it is preferred that said methods comprise cloning, sequencing and transformation of recombinant nucleic acids. For this purpose appropriate vectors, primers, enzymes, host cells and the like can be used and are known by the skilled artisan. Preferably, genetically engineered cells comprise cells harbouring recombinant nucleic acids encoding antigens or immunogens or parts thereof, cytokines, chemokines, growth factors and the like. Antigens and immunogens can be, for example, one or more tumour antigens or parts thereof, antigens from infectious microorganisms or parasites, like bacteria, fungi, viruses and the like. Furthermore, among the immunogens are, for example, molecules which increase the immunogenicity, like pan T-cell epitopes or multimers thereof, like PADRE-epitopes, or tetanus toxoid fragments which evoke an additional immunstimulatory effect via activation of MHC class II-mediated processes. It is also envisaged that the cells of the cell lines of the present invention are genetically engineered with nucleic acids encoding effector molecules, like transcription factors, components of signal transduction pathways or signalling cascades, or cytokines, chemokines, growth factors and the like which are able to modulate directly or indirectly the expression of endogenous molecules, e.g. nucleic acids, polypeptides, posttranslationally modified polypeptides and lipids and the like. More preferably, the tumour cells are transiently or stably transfected with a desired nucleic acid molecule.

It is also envisaged that the cells of the cell lines of the present invention are genetically engineered so as to express a polypeptide against which antibodies should be raised. If cell lysates from these tumour cells are produced and administered to an individual, it is expected that a humoral and/or cellular immune response is developed by individuals, preferably this immune response comprises antibody responses and/or T helper cell responses and/or cytotoxic T cell responses more preferable is combination of humoral and cellular immune responses.

In accordance with the present invention, the term "mutated" means (a) permanent modification(s) of genetic material, i.e. nucleic acids, caused, for example, naturally or by physical means or chemical compounds/substances/agents such as EMS. Said modifications include point mutations, like transitions or transversions, deletion/insertion/addition of one or more bases within a nucleic acid/gene/chromosome thereby modifying the nucleic acid/gene/chromosome which can cause, inter alis, aberrant gene expression/transcription/translation or inactive gene products, constitutive active/inactive gene products leading to e.g. dominant-negative effects. Thus, it is also envisaged that the cells of the cell lines of the present invention comprise cells which harbour (a) mutation(s) in (a) desired gene(s) or in which (a) mutation(s) in (a) desired gene(s) is induced by methods known to the person skilled in the art. It is also known in the prior art that mutated or genetically engineered tumour cells can be selected by any suitable method/phenotype.

In accordance with the present invention the term "infected" means cells of the cell lines of the present invention, which have been infected with a virus, or viroid, and/or proteinaceous structure. Said virus, or viroid, and/or proteinaceous structure may also be used as a vehicle for genetically engineering said cells. It is preferred that said virus which infects tumour cells is an oncogenic virus, however, is not limited to oncogenic viruses. Most preferably said oncogenic virus is selected from the group consisting of retroviruses or DNA viruses, e.g. papovaviruses like human papilloma viruses (HPV), type C oncoviruses, like human T cell leukaemia viruses (HTLV), herpes viruses, like Epstein-Barr virus (EBV), hepadnaviruses, like hepatitis B virus (HBV), and lentiviruses, like human deficiency virus (HIV). It is also envisaged that tumour cells are already infected with any one of the above mentioned viruses. Furthermore, infected tumour cells or lysates thereof may be important when used for prophylactic/therapeutic vaccination against infectious diseases caused for example by viruses like HIV, HBV, hepatitis C virus (HCV), HPV. Preferably, the infectious component(s) comprised by the lysates produced from these infected cells has/have to be additionally inactivated. Methods to be used are known to those skilled in the art, e.g., heat inactivation, acid inactivation and/or sterile filtration or the like.

In another aspect, the present invention relates to a lysate of the cell lines of the present invention.

According to the present invention the term "lysate" means a solution or suspension in an aqueous medium of the cells of the present invention, wherein at least 50%, preferably 75% and most preferred more than 95%, e.g. 99% or most preferred 100% of the cells are broken. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. Preferably the lysate is devoid of all or most of the DNA. The preparation of such lysates and fractions thereof are known to those skilled in the art. The details of the preparations of such cell lysates as well as for the preparation of heat induced cell lysates are specifically described in a PCT-application filed on Aug. 18, 2003 on behalf of the NEMOD Immuntherapie AG and based on EP 02 01 8512. Accordingly, those skilled in the art are readily in a position to prepare the desired lysates by referring to the above general explanations and specific explanations in EP 02 01 8512.

Furthermore, the present invention relates to molecules, a mixture of molecules or fragments hereof obtained from the cell lines of the present invention.

According to the present invention the term "molecules" means biomolecules obtained from the cells of the present invention. These biomolecules can be for example proteins, glycoproteins, or glycolipids and can be obtained by suitable fractionation techniques, for example a single or combination of various chromatography in order obtain the molecule or a mixture of desired molecules. The techniques for fractionations and purification steps are well known to those skilled in the art. Molecules can be obtained from the media for example from secreted molecules or by preparation from cells, for example from membranes, cytoplasm, nucleoplasm or comparments like the endoplasmaticreticulum/golgi apparatus. Examples are MUC1 obtained from the media whereby NM-D4 is preferred before NM-F9 as a source. This MUC1 carries TF groups and the TA-MUC1 epitope (table 2) and is immunostimulatory. Another example is the generation of AGPA (asioaloglycophorin) from membrane preparations whereby NM-F9 is preferred over NM-D4. The yield of the latter can be increased for example by using an expression vector for transfection of the glycophorin A. Soluble AGPA can be generated by transfection of a vector encoding glycophorin A without transmembrane and intracellular parts but with secretory signals.

Furthermore, the present invention relates to dendritic cells loaded with the lysate of the present invention.

In accordance with the present invention the term "dendritic cells" relates to professional antigen-presenting cells which capture antigens and migrate to the lymph nodes and spleen, where they are particularly active in presenting the processed antigen to T cells. The term "dendritic cells" also means cells which have an activity and function similar to dendritic cells. Dendritic cells can be derived from either the lymphoid or mononuclear phagocyte lineages. Said dendritic cells can be found in lymphatic and non-lymphatic tissue. The latter appear to induce a T cell response only when being activated and having migrated to lymphatic tissues. Dendritic cells are known to be the or amongst the most potent activators and regulators of immune responses. One important feature is that they are presently the only antigen presenting cells known to stimulate naïve T cells. Immature dendritic cells are characterized by their ability to take-up and process antigens, a function that is dramatically reduced in mature dendritic cells, which in turn exhibit enhanced presentation of processed antigens on their surface, mainly bound to MHC Class I and Class II molecules but also via CD1 molecules. Maturation is also associated with upregulation of costimulatory molecules (such as CD40, CD80 and CD86), as well as certain other cell surface proteins (e.g. CD83 and DC-Sign). Dendritic cell maturation is also usually associated with enhanced migratory capacity, resulting (in vivo) in migration of dendritic cells to the regional lymph nodes, where the dendritic cells encounter T and B lymphocytes. Dendritic cells can be obtained from individuals using methods known to those skilled in the art and are described in more detail in the examples herein. Furthermore, according to the invention, dendritic cells are also those cells or cell lines which show the comparable functional and/or phenotypic features as dendritic cells, e.g. MUTZ-3 derived cells.

Dendritic cells or their precursors are differentiated using suitable growth factors and/or cytokines, e.g. GM-CSF and IL-4 as shown in the examples herein, the resulting immature dendritic cells are loaded with a lysate according to the invention. Immature DC (iDC) loaded with a lysate according to the invention are further maturated to mature DC (mDC). In special cases also mDC can be loaded (pulsed) with antigens or immunogens from the lysate. Vaccine compositions or pharmaceutical compositions for preventing or treating cancers, tumourous diseases and or infectious diseases preferentially comprise loaded mDC which originate from loaded and matured iDC or which were loaded after or during maturation. The dendritic cells can be loaded either with lysates, fractions from lysates, a molecule or a mixture of molecules or fragments hereof originating from NM-F9 and/or NM-D4. In addition, dendritic cell can be loaded by co-incubation or fusion with cells from these cell lines.

A further embodiment of the present invention is a composition comprising the cell lines, the lysate, molecules, mixtures of molecules and/or the dendritic cells of the present invention.

Figure 5:
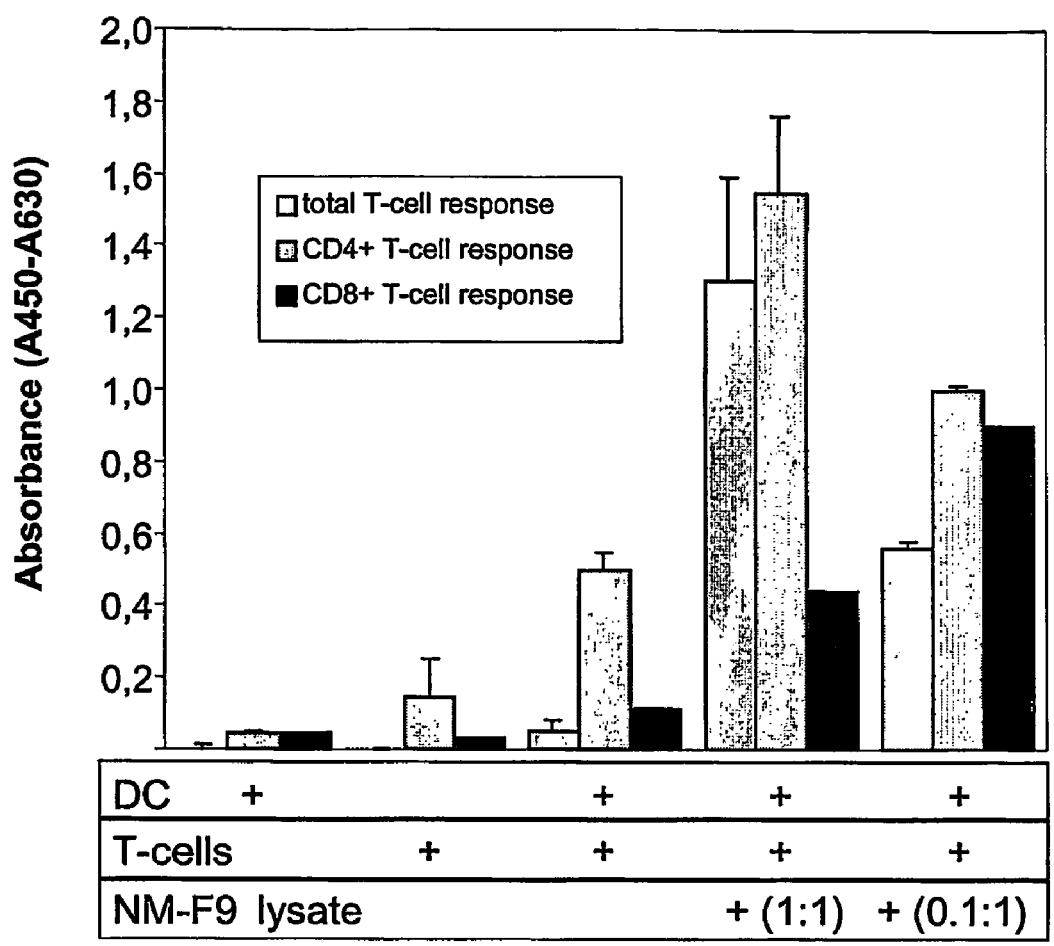

In order to investigate the potential of NM-F9 lysates to induce cellular and humoral immune responses following assays were performed: It could be shown in vitro that T-cell proliferation was induced when cocultivated with mature monocyte derived DC loaded with NM-F9 cell lysates (FIG. 5). The DC were loaded with the lysate in the immature state and further maturated which leads to antigen uptake, processing and presentation in the context of MHC class I and II molecules on mature DC (hmoDC). This immunogenic effect of NM-F9 cell lysates was observed for total T-cells, CD4+ T helper cells and cytotoxic CD8+ T-cells.

Figure 6:
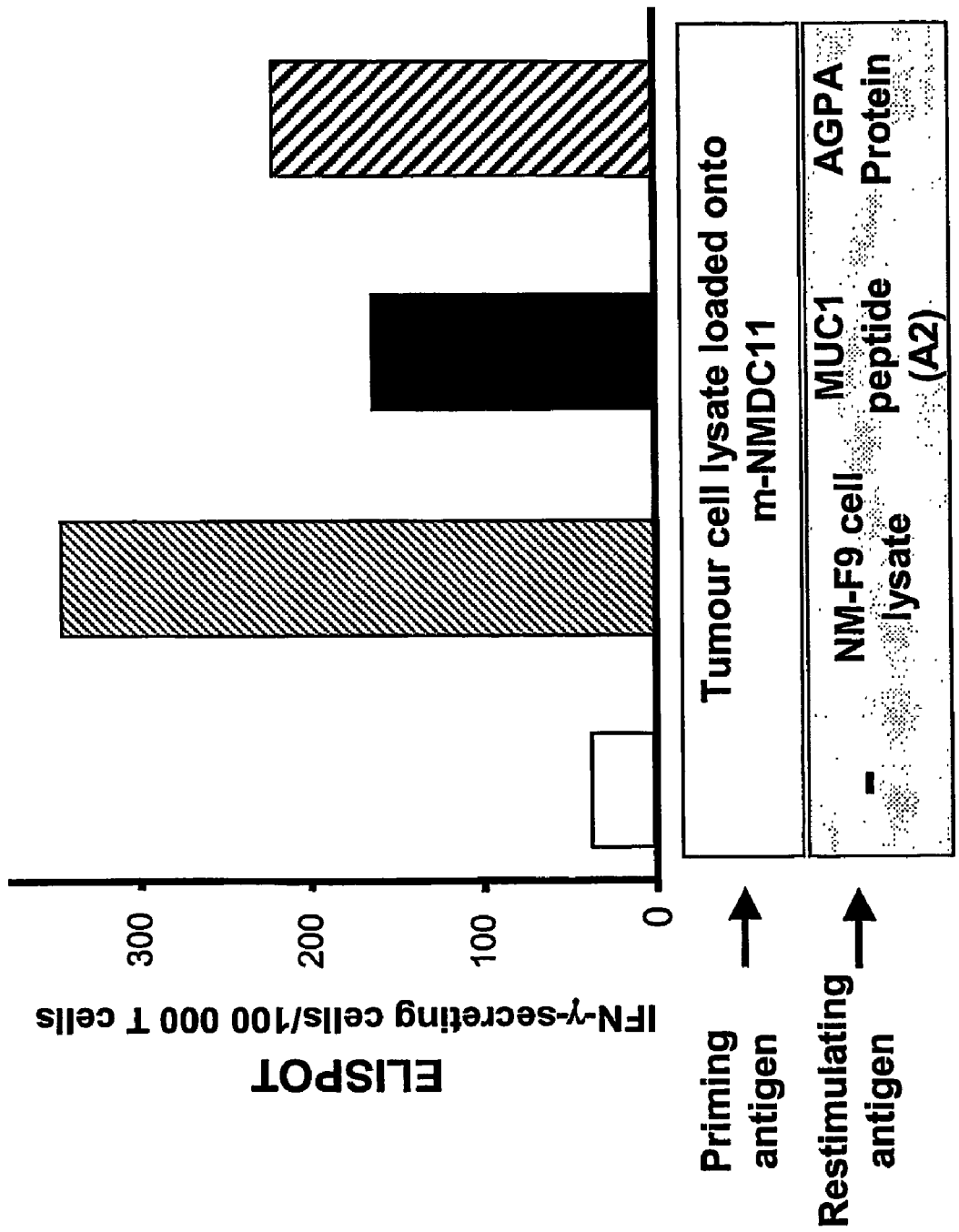

Activation of specific naïve cytotoxic T cells against MUC1 and AGPA were tested with functional mature human dendritic cells m-NMDC11 loaded with NM-F9 lysates in the prime reaction and restimulation with m-NMDC11 loaded with a MUC1 A2 peptide and AGPA protein respectively, showing that naïve CTL can be activated against these antigens using NM-F9 (FIG. 6). NMDC11 is an optimized MUTZ-3 derived fully functional human dendritic cell line with features as described in WO03/023023.

Induction of an antibody response towards the several antigens was tested in NOD/SCID mice reconstituted with human PBMC that were vaccinated with NM-F9 cell lysates. Surprisingly, an antibody response in form of human IgM but also IgG could be observed against TF, Tn, MUC1 and AGPA (table 3). The induction of an IgG response indicates a switch of antibody class associated with a T helper cell immune response as well as induction of memory immune responses against the above antigens including the carbohydrate antigens.

Accordingly, in a preferred embodiment, said composition is a pharmaceutical composition. The cells which were tested to be virus free are conventionally grown in media, preferably serum free media. Cell are harvested by conventional means and transferred in suitable solutions for application which are described in more detail below. Cells are either used fresh or after deep-freezing and re-thawing in special freezing medium known to skilled persons, whereby some loss in vitality is normal, in a living fashion preferably after lethal irradiation which prevents proliferation, or as lysates generated as described and cited above, or in form of molecules or mixtures of molecules generated and purified as described elsewhere here. Such pharmaceutical compositions comprise a therapeutically effective amount of the cell lines, the lysate, molecules, mixtures of molecules and/or the dendritic cells of the present invention, and a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the cell lysate, preferably in purified form, together with a suitable amount of carrier so as to provide the form for proper administration to the patient. The formulation should suit the mode of administration.

In another embodiment, the composition is formulated in accordance with routine procedures as a pharmaceutical composition adapted for intravenous administration to human beings. Typically, compositions for intravenous administration are solutions in sterile isotonic aqueous buffer. In a preferred embodiment, the pharmaceutical compositions are in a water-soluble form, such as pharmaceutically acceptable salts, which is meant to include both acid and base addition salts. The administration of the candidate agents of the present invention can be done in a variety of ways as discussed above, including, but not limited to, orally, subcutaneously, intravenously, intranasally, transdermally, intranodally, peritumourally, intratumourally, intrarectally, intraperitoneally, intramuscularly, intrapulmonary, vaginally, rectally, or intraocularly. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The amount of the cell-lines, the cell lysate and/or the dendritic cells of the present invention which will be effective in the treatment or prevention (in particular by vaccination) of cancers, tumours and/or tumourous diseases can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

In a further preferred embodiment, the composition of the present invention is a vaccine composition.

In accordance with the present invention the term "vaccine composition" relates to any composition which can be used as a vaccine. A vaccine means a therapeutic or prophylactic use of the pharmaceutical composition which induces an immune response. The forms or methods for manufacturing vaccine compositions according to the present invention are not particularly limited, and a composition in a desired form can be prepared by applying a single method available in the field of the art or methods in an appropriate combination. For the manufacture of a vaccine composition, aqueous media such as distilled water for injection and physiological saline, as well as one or more kinds of pharmaceutical additives available in the field of the art can be used. For example, buffering agents, pH adjusting agents, solubilizing aids, stabilizing agents, soothing agents, antiseptics and the like can be used, and specific ingredients thereof are well known to those skilled in the art. The vaccine composition can also be prepared as a solid preparation such as a lyophilized preparation, and then prepared as an injection by adding a solubilizing agent such as distilled water for injection before use. Depending upon the manner of introduction, the compounds may be formulated in a variety of ways as discussed below. The concentration of therapeutically active compound in the formulation may vary from about 0.1-100 wt %. The vaccine composition may be administered alone or in combination with other treatments, i.e., radiation, or other chemotherapeutic agents or anti-cancer agents. In a preferred embodiment, the vaccine compositions are in a water-soluble form, such as pharmaceutically acceptable salts, which is meant to include both acid and base addition salts. The vaccine compositions can be prepared in various forms, such as injection solutions, suspensions, and the like. The vaccine compositions may also include one or more of the following: carrier proteins such as serum albumin; buffers; stabilizing agents; colouring agents and the like. Additives are well known in the art, and are used in a variety of formulations. A vaccine composition according to the present invention is preferably used for immunization against cancer and/or tumourous diseases.

In another embodiment the pharmaceutical or vaccine composition according to the present invention further comprises cell and/or lysates of a heterologous cell. The term "lysates" was already explained herein before.

When used in the context of the present invention the term "heterologous cell" means a cell which is not identical to the cells of the cell lines of the present invention. Notably, said heterologous cell can be autologous, allogeneic or xenogenic to the individual to which it may be applied. In the context of the present invention the term "autologous" means that the heterologous cells are derived from the same individual to which the pharmaceutical or vaccine composition according to the invention shall be later administered. In accordance with the present invention the term "allogeneic" means that the heterologous cells are derived from an individual which is different from the individual to which the pharmaceutical or vaccine composition according to the present invention shall be later administered. The term "xenogenic" means that the heterologous cells comprise cells which are not originating from the same species to which they shall be later administered in the from of the pharmaceutical or vaccine composition according to the present invention. It is envisaged that said heterologous cell is, for example, a tumour cell derived from a tumour or metastases, also including micrometastases which can, e.g., be obtained by surgery, biopsy, or the like. The tumour cells can be derived from any possible type of tumours.

Examples for such heterologous tumor cells as well as indications for which the inventory pharmaceutical or vaccine compositions can be used are exemplified in the following: Examples are skin, breast, brain, cervical carcinomas, testicular carcinomas, head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis, a immunosuppression-related malignancy and/or metastatic cancer etc. The tumour cells may, e.g., be derived from: head and neck, comprising tumours of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the oesophagus, stomach, pancreas, liver, biliary tree, small intestine, colon, rectum and anal region, a cancer of the genitourinary system, comprising cancer of the kidney, urethra, bladder, prostate, urethra, penis and testis, a gynaecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumour of the thyroid, parathyroid, adrenal cortex, pancreatic endocrine tumours, carcinoid tumour and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumour, neurofibromatoses, neuroblastoma, Ewing's sarcoma family of tumours, rhabdomyosarcoma, a lymphoma, comprising non-Hodgkin's lymphomas, cutaneous T-cell lymphomas, primary central nervous system lymphoma, and Hodgkin's disease, a leukaemia, comprising acute leukemias, chronic myelogenous and lymphocytic leukemias, plasma cell neoplasms and myelodysplastic syndromes, a paraneoplastic syndrome, a cancer of unknown primary site, a peritoneal carcinomastosis, a immunosuppression-related malignancy, comprising AIDS-related malignancies, comprising Kaposi's sarcoma, AIDS-associated lymphomas, AIDS-associated primary central nervous system lymphoma, AIDS-associated Hodgkin's disease and AIDS-associated anogenital cancers, and transplantation-related malignancies, a metastatic cancer to the liver, metastatic cancer to the bone, malignant pleural and pericardial effusions and malignant ascites. It is mostly preferred that said cancer or tumourous disease is cancer of the head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis, a immunosuppression-related malignancy and/or metastatic cancer. Accordingly, the term "indications" "tumour as provided herein, includes individual afflicted by any one of the above-identified conditions at any stage of development, but is not limited to the mentioned conditions.

Preferably, the aforementioned heterologous cells have one or more antigens which are shared with the cancers or tumorous diseases to be treated. The advantage is an additional strong response against antigens or immunogens foreign to the cancers or tumorous diseases to be treated or prevented, e.g., antigens specific for the tumor cell which are not shared by the cancer or tumors to be treated or prevented, comprising a strong danger signal and/or helper response which can be favourable to overcome anergies and/or tolerances. In a preferred embodiment the tumor cells are in addition from an allogeneic source which can in addition have a strong allo-response which can be further favourable to overcome anergies and/or tolerances.

Preferably, the aforementioned pharmaceutical or vaccine compositions comprises NM-D4 and/or NM-F9 sharing one or more antigens with the cancers or tumourous diseases to be treated. The advantage of the allogeneic origin of NM-F9 and/or NM-D4 for the individual to be treated is an additional strong response against antigens or immunogens foreign to the cancers or tumourous diseases to be treated or prevented, e.g., antigens tumour which are not shared by the cancer or tumours to be treated or prevented, and because of the allogenicity a strong alloresponse in general comprising a strong danger signal and/or helper response which can be favourable to overcome anergies and/or tolerances tumour.

In another preferred embodiment the pharmaceutical or vaccine composition of the present invention further comprises an adjuvant.

With respect to the present invention the term "adjuvant" means that the natural ability of an antigen to induce an immune response can be modified, and in particular enhanced, by altering or by mixing it or loaded dendritic cells described hereinabove with another substance. The term "adjuvant" also means that tumour cells from which the lysates are generated and/or dendritic cells are genetically modified in order to express adjuvants or costimulatory factors. The procedure or the substance used to enhance immune responses is called an adjuvant. At least three classes of adjuvants have been used for a long time; these are mineral oil emulsions, aluminium compounds, and surface active materials such as saponin, lysolecithin, retinal, Quil A®, some liposomes, and pluronic polymer formulations. See, for example, Fundamental Immunology, edited by William E. Paul, at p. 1008, Raven Press, New York (this book will hereinafter be referred to as "Fundamental Immunology"). Aluminium adjuvants used alone or in combination include aluminium hydroxide gel, aluminium phosphate, aluminium sulphate, and alums comprising ammonium alum (such as $(NH_4)_2 SO_4 Al_2 (SO_4)_3$) and potassium alum. Aluminium hydroxide (hereinafter "AL") is one of the older adjuvants and it is considered so safe that it has been applied in bacterial and viral vaccines administered to billions of people around the world. Calcium phosphate gel (hereinafter "CP") has similar properties and is also used in vaccines. Both substances are available in pharmaceutical qualities in most countries worldwide. Techniques for preparing adjuvant-antigen preparations for injection are well known in the art. See, for example, Terry M. Phillips, Analytical Techniques in Immunochemistry, pp. 307-10, Marcel Dekker, New York, 1992. Other adjuvants include complete Freund's adjuvant (a water-in-oil emulsion in which killed, dried, mycobacteria—usually *M tuberculosis*—are suspended in the oil phase); incomplete Freund's adjuvant (analogous to the complete Freund's adjuvant with no mycobacteria); ISCOM (or immune stimulating complex, comprising lipophilic particles formed by the spontaneous association of cholesterol, phospholipid and the saponin Quil A®); lipopolysaccharide (complex molecules consisting of a lipid core—lipid A—with a polysaccharide side chain that are components of certain bacilli, Lipid A is incorporated into the outer membrane of the bacterium and the polysaccharide projects extracellularly. Their adjuvant potency is associated with lipid A; they are also mitogenic for murine B lymphocytes); and mycobacterial adjuvants (whole, heat killed, dried, mycobacteria—such as *M. tuberculosis, M. avium, M. phlei*, and *M. smegmatis*) that, when suspended in mineral oil and emulsifier, have adjuvant activity with respect to any antigen given with them. Extracts of some mycobacteria, e.g., mycobacterial peptidoglycolipids have similar adjuvant activities. See, for example, Dictionary of Immunology at pp. 3, 7, 46, 94, 97, 105, and 116; R. B. Luftig, Microbiology and Immunology, pp. 228-29, Lippincott-Raven Publishers, Philadelphia 1998. Microbial adjuvants include *Corynebacterium parvum* and *Bordetella pertussis*. See, for example, Handbook of Immunology at 115-16. Use of controlled-release preparations and materials with adjuvant activity and possible sites of action have been described in Fundamental Immunology at pp. 1007-09. Mineral carriers such as aluminium hydroxide, potassium ammonium sulphate, and potassium aluminium sulphate adsorb the antigen on their surface. These common adjuvants have been used at a 0.1% concentration with up to 1 mg protein antigen in 1 ml administered to animals at doses of 0.2-0.5 ml/(kg body weight). See Miroslav Ferencik, Handbook of Immunochemistry, p. 115, Chapman & Hall 1993 (this book will hereinafter be referred to as "Handbook of Immunochemistry"). Although Freund's adjuvant is toxic and not used for immunization of human beings, mineral adjuvants such as aluminium hydroxide are common in human medicine. Id. at 116. In addition to alum, other adjuvants in the group of inert carriers include bentonite, latex, and acrylic particles. See Fundamental Immunology at 1008. Combinations of adjuvants can also have adjuvant properties. For example, it has been shown that the combination of saponin and muramyl dipeptide in a squalene in water emulsion is superior to alum as an adjuvant for inducing certain responses in mice. R. Bomford, M. Stapleton, S. Wilson, A. McKnight, and T. Andronova, The control of the antibody isotype responses to recombinant human immunodeficiency virus gp120 antigen by adjuvants, AIDS Res. Hum. Retroviruses Vol. 8 (1992) pp. 1765 et seq. These adjuvants are complemented by new adjuvants that have been developed during the last fifteen years. See, for example, Anthony C. Allison, The Role of cytokines in the Action of Immunological Adjuvants, in Vaccine Design. The Role of cytokine Networks, edited by Gregory Gregoriadis and Brenda McCormack, NATO ASI Series A: Life Sciences Vol 293, pp. 1-9, Plenum Press, New York 1997 (this book will hereinafter be referred to as "Vaccine Design"); Immunology at p. 116; H. Snippe, I. M. Fernandez and C. A. Kraaijeveld, Adjuvant Directed Immune Specificity at the Epitope Level. Implications for Vaccine Development. A Model Study Using Semliki Forest Virus Infection of Mice, in Vaccine Design at pp. 155-73. An adjuvant can be administered prior to, simultaneously with, or following the administration of the antigen. Antibody production enhancement caused by adjuvants is not fully understood. However, adjuvant properties that may exist either alone or in various combinations and which permit a substance or formulation to be described as adjuvant active have been defined. See, for example, J. C. Cox and A. R. Coulter, Adjuvants—A classification and review of their modes of action, Vaccine Vol. 15 (1981) pp. 248 et seq.; John Cox, Alan Coulter, Rod Macfarlan, Lorraine Beezum, John Bates, Tuen-Yee Wong and Debbie Drane, Development of an Influenza-ISCOM™ Vaccine, in Vaccine Design at pp. 33-49. One of these properties is depot generation, whereby the vaccine is retained near the dose site to give short-term trickle release or a longer term pulsed release. Id. at p. 34.

Preferably, the pharmaceutical or vaccine composition is administered directly or in combination with an adjuvant mentioned herein above and/or loaded on antigen-presenting cells, particularly dendritic cells. It is also preferred that both the pharmaceutical or vaccine composition and the adjuvant and the pharmaceutical or vaccine composition and the loaded dendritic cells are administered together or separately from each other e.g. at different time points or at different locations. Additionally, it is also preferred that said pharmaceutical composition and adjuvant is administered together with said pharmaceutical composition loaded on dendritic cells. Since dendritic cells are highly specialized antigen-presenting cells with the unique capability in initiating and regulating antigen-specific immune responses, it is preferred to combine them with the pharmaceutical or vaccine compositions of the present invention. For the preparation of a tumour vaccine dendritic cells can be generated from the peripheral blood of tumour patients from other donors or from the above-mentioned cell lines. In clinical studies, the efficacy of vaccination with dendritic cells has been demonstrated using immunological and—in some cases—clinical endpoints.

Active specific immunotherapy approaches to the treatment of tumours have been widely investigated during recent years. Numerous studies involving the vaccination of patients with their own inactivated tumour cells have been reported. These studies have demonstrated that inclusion of an adjuvant is necessary to stimulate the patient's immune system especially against the autologous, or derived from self, tumour cells. For example, methods utilizing the particulate adjuvant, *Bacillus* Calmette-Guerin (BCG) cells, administered systemically or mixed with the patient's own tumour cells have been shown to induce tumour-specific immunity in laboratory animals. Peters, L. C., Brandhorst, J. S., Hanna Jr., M. G., Preparation of Immuno-Therapeutic Autologous Tumour Cell Vaccines from Solid Tumours; Cancer Res. 39: 1353-1360 (1979).

In another preferred embodiment the dendritic cells used in the aforementioned compositions are loaded mature dendritic cells (mDC) which originate from lysate-loaded and further matured immature dendritic cells (iDC) or which were loaded after or during maturation. The term "immature" when used in accordance with the present application relates to professional antigen-presenting cells that are characterized by their ability to take-up and process antigens. The term "mature" when used in accordance with the present application relates to professional antigen-presenting cells that express costimulatory factors and antigens in the context of MHC class molecules or CD1 molecules and can activate T cells, regulatory NKT cells and/or B cells.

Mature DC loaded with the lysate according to the invention are preferably used to treat or prevent tumourous or infectious diseases. It is also envisaged that the DC were loaded with a molecule or a mixture of molecules obtained from NM-F9 and/or NM-D4, co-incubated or fused with NM-F9 and/or NM-D4 cells.

Moreover, the present invention relates to a method for the production of a vaccine composition comprising the step of combining a cell line, or a lysate, molecule or mixture of molecules obtained from these cell lines, or dendritic cells loaded with said lysate, co-cultivated or fused with cells from the cell lines according to the present invention with an adjuvant The present invention also relates to a method for the production of a pharmaceutical composition comprising the step of combining a cell line, or a lysate, molecule or mixture of molecules obtained from these cell lines, or dendritic cells loaded with said lysate, co-cultivated or fused with cells from the cell lines according to the present invention with a pharmaceutically acceptable.

In another aspect the present invention relates to a method for the treatment or prevention, e.g. by vaccination, of cancer and/or tumourous diseases in an individual comprising the step of administering to the individual a therapeutically or prophylactically effective amount of the cell line, the pharmaceutical or vaccine composition or the dendritic cells according to the present invention.

In the context of the present invention the term "individual" means a subject in need of a treatment or prevention of cancer and/or tumourous diseases. Preferably, the subject is a vertebrate, even more preferred a mammal, particularly preferred a human. If the subject is not a human the inventive cell lines; lysates, molecules or mixture of molecules are used in a xenogenic fashion. In the case of dendritic cells are the dendritic cells of the origin of the species it is used at.

The term "administered" means administration of a therapeutically or prophylactically effective dose of the cell lysate of the invention to an individual. By "therapeutically or prophylactically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In accordance with the present invention the term "vaccination" is related to a general process for immunization against cancers and/or tumourous diseases. Vaccination is a form of deliberate artificial immunization whereby the cell-lines; cell lysates, molecule, or mixture of molecules and/or dendritic cells of the present invention are administered. The cell-lines; cell lysates, molecule, or mixture of molecules and/or dendritic cells are administered in a form as described herein, supra, and may sensitise the immune system such that if cancer, tumourous diseases, infections and/or automimmune diseases arise within the body are being treated or prevented. See, for example, Immunology, at pp. 87-88; AMA Encyclopedia of Medicine at 573-574 and 1034; S. J. Cryz, Jr., in Immunotherapy and Vaccines, edited by Stanley J. Cryz, pp. 3-11, VCH, Weinheim, Germany 1991. For an overview of the immune system from a molecular perspective, see, for example, Mary S. Leffell, An Overview of the Immune System: The Molecular Basis for Immune Responses, in Human Immunology Handbook pp. 1-45. Vaccination is also associated with immunization.

Immunization is a general term, and the term vaccination is used when patients are immunized. In general, immunization can be used as, a preventive or as a therapeutic treatment. The preventive use of immunization is a prophylactic treatment, whereas the use of immunization while the disease is in progress is immunotherapy. Immunization provides two types of acquired immunity, active and passive. Immunotherapy is the treatment of a disease by immunization, active or passive, or by the use of agents that modify the actions of lymphocytes. In particular, immunotherapy refers to the stimulation of the immune system and conventionally uses a form of immunostimulant, a substance that causes a general, non-specific, stimulation of the immune system. The American Medical Association Encyclopedia of Medicine, p. 576 (this encyclopedia will hereinafter be referred to as "AMA Encyclopedia of Medicine").

In a method for inducing an immune response to treat or prevent cancer and/or tumourous diseases, the cell lines of the present invention and/or cell lysates and/or molecule and/or mixture of molecules and/or dendritic cells according to the invention are provided, and an effective amount of the cell lines; the cell lysates, the molecule, the mixture of molecules, and/or the dendritic cells are injected at least once so as to permit release of biologically active quantities of the immunostimulant over a period of time to induce an immune response to the presence of active tumour cells.

An individual for the purposes of the present invention includes both humans and other animals, preferably vertebrates and more preferably mammals. Thus the methods are applicable to both human therapy and veterinary applications. In a preferred embodiment the individual is a mammal, e.g. a mouse, and in a most preferred embodiment the individual is human.

The compounds described herein having the desired therapeutic or prophylactic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt % However, it is also envisaged that the person skilled in the art is readily in a position to determine the concentration of the therapeutically active compound in the formulation by using his common general knowledge. The agents maybe administered alone or in combination with other treatments, i.e., radiation, or other chemotherapeutic agents.

In a preferred embodiment, the pharmaceutical compositions are in a water-soluble form, such as pharmaceutically acceptable salts, which is meant to include both acid and base addition salts.

The administration of the candidate agents of the present invention can be done in a variety of ways as discussed above, including, but not limited to, orally, subcutaneously, intravenously, intranasally, transdermally, intranodally, peritumourally, intratumourally, intrarectally, intraperitoneally, intramuscularly, intrapulmonary, vaginally, rectally, or intraocularly.

The cells of the cell line, lysates, molecule, mixture of molecules or therewith loaded or fused dendritic cells in form of a pharmaceutical or vaccine compositions can be administered to the subject at a suitable dose. Administration of the suitable compositions may be effected by different ways, e.g., by intravenous, intraperitoneal, subcutaneous, intramuscular, topical, intradermal, intranasal, intranodal, intrarectal, peritumoral, intratumoral or intrabronchial administration. The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose of lysate originates from about 1000 to $10^{13}$ cells and the typical dose for dendritic cells is about $10^4$ to $10^{12}$ cells, however, doses below and above this exemplary range are envisaged. Preferably, the dose of lysate or molecules corresponds to amounts generated from cells numbers between $10^4$ to $10^{12}$ cells, more preferably between $10^5$ to $10^{11}$ cells, more preferably between $10^6$ to $10^{10}$ cells. Preferably, the dose for loaded dendritic cells is between $10^5$ to $10^{11}$ cells, more preferably between $10^6$ to $10^9$ cells. Amounts for molecules can vary between 0.1 µg and 10 g. Doses can vary between individuals and can be split to multiple injections at different sites and/or administration routes. Suitable and optimal doses can be determined by those skilled in the art. The amount of cell lysate used for loading dendritic cells can be determined by those skilled in the art, for example by those in vitro and or in vivo assays which are exemplary shown in the examples. Preferable amounts for lysates and molecules for loading dendritic cells originate from $10^3$ to $10^{13}$ cells, more preamble from $10^4$ to $10^{12}$ cells, more preferable from $10^5$ to $10^{11}$ cells, and more preferably from $10^6$ to $10^{10}$ cells. Generally, the regimen as a regular administration of the pharmaceutical or vaccine composition should be in the range of 0.1 µg to 10 g per dose for the lysates and molecules, preferably 50 to 100 mg, amounts for fractionated lysates can be correspondently lower but may reach the high amounts. The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition.

If the regimen is a continuous infusion, it should also be in the range of 1 µg to 10 mg per kilogram of body weight per minute, respectively. Progress can be monitored by periodic assessment. The cell lines, cell lysates, molecules and/or dendritic cells of the invention may be administered locally or systemically. Administration will preferably be parenterally, e.g., intravenously, intranodally, intra peritoneally, intra tumourally, peritumourally. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

It is also envisaged that the cells of the cell lines, lysates, molecules or loaded dendritic cells or compositions are employed in co-therapy approaches, i.e. in co-administration with other medicaments or drugs, for example anti-cancer drugs. When vaccine therapy is carried out using the cells of the cell lines, lysates, molecules or mixture of molecules or loaded or fused dendritic cells of the present invention, they may be administered only once. However, it is desirable to repeat the administration to the same site of a body to achieve coexistence of a tumour antigen and a cytokine or a cytokine-inducing agent as long as possible. For example, both components may preferably coexist for 3 hours or more so that inflammatory reaction at the site of administration can be induced and conditions can be achieved wherein immune cells are concentrated and cells are kept at the site. When cells, a cell lysate, molecules or loaded or fused dendritic cells of invention are administered without adjuvant, an adjuvant may be administered to the same or distant site. Generally, the vaccine can be administered to a patient bearing a tumour that contains, from a viewpoint of pathological diagnosis, the same or relative species of one or several tumour antigens as that contained in the pharmaceutical or vaccine composition or it can even be use in cases where no shared tumour antigens occur. The latter case may use bystander immunological effects including for example alloresponses. The site to be administered is not particularly limited and can be for example orally, subcutaneously, intravenously, intranasally, transdermally, intranodally, peritumourally, intratumourally, intrarectally, intraperitoneally, intramuscularly, intrapulmonary, vaginally, rectally, or intraocularly. The dose and administration period of the tumour vaccine of the present invention are not particularly limited. It is desirable to determine an appropriate dose and administration period by observing effects of the vaccine therapy. The administration can be made, for example, by injections and the like.

The invention also relates to the use of one or more cell lines, the lysate, a molecule or a mixture of molecules obtained therefrom or dendritic cells loaded or fused therewith according to the invention for the preparation of a vaccine or pharmaceutical composition for the treatment or prevention of cancer and/or tumourous diseases.

The term "cancer and/or tumourus diseases" preferentially relates to such cancers or tumourous diseases which are characterized by tumour cells which express either TF, MUC1, preferably TA-MUC1, Tn and/or LeX on the cell surface. As described above tumours which have at least one of those antigens are preferred. Most preferred are those which have at least two of those antigens shared and more preferred those with three and even more those with all of the above described antigens. However, also tumours or tumour of an individual can be successfully treated where non of those above mentioned antigens are shared due to the allogeneic nature of the approach and the therewith connected strong alloresponse which may enable the breaking of tolerances and anergies as well as the lack of immunoinhibitory features of the MUC1 (TA-MUC1) on the cell lines. In a preferred embodiment the cancer or tumourous disease to be treated or prevented is a cancer/tumourous disease of the head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis, a immunosuppression-related malignancy and/or metastatic cancer. More preferred are the carcinoma indications included above. However, said cancer/tumourous disease may also be selected from those mentioned hereinabove in connection with the process according to the invention.

In view of the in vivo and in vitro results of the examples of the present invention it is expected that the invention provides an advantageous cancer and/or tumourous disease vaccine. Recognized preclinical studies showed that the cell lines of the invention can be used in order to induce a specific cellular and humoral immune response. Human specific cytotoxic and helper T cells could be induced. Specific human and murine antibodies, IgM and IgG, against TF, Tn, MUC1 and AGPA, could be induced in mice as well as in NOD-SCID mice with a reconstituted human immune system showing the potency, specificity of the approach including anti-carbohydrate immune responses including T cell responses The Figures show:

FIG. 1 Immuncytochemical analysis of antigen expression in NM-F9 and K562-wt cells. K562 cells were selected for TF expression and subcloned for stabilization of TF expression. One representative subclone (NM-F9) and the original K562 wild type (wt) cells were stained with A78-G/A7 (anti-TF), HB-Tn 1 (anti-Tn), A83-C/B12 (anti-GPA), A63-C/A9 (anti-AGPA) and PankoMab (anti-MUC1) and analysed by immunfluorescence microscopy.

FIG. 2 Cell surface expression of antigens on and K562-wt cells. K562-wt and NM-F9 cells were stained with A78-G/A7 (anti-TF), HB1-Tn (anti-Tn), HB1-sTn (anti-sTn), A83-C/B12 (anti-GPA), A63-C/A9 (anti-AGPA), PankoMab (anti-MUC1), anti-CD15 (anti-Lewis$^x$) and anti-sialyl-Lewis$^x$. Cells were analysed by flow cytometry. Additionally cells were sialidase treated and analysed for AGPA (A63-C/A9) and TF(A78-G/A7) expression.

Figure 3:
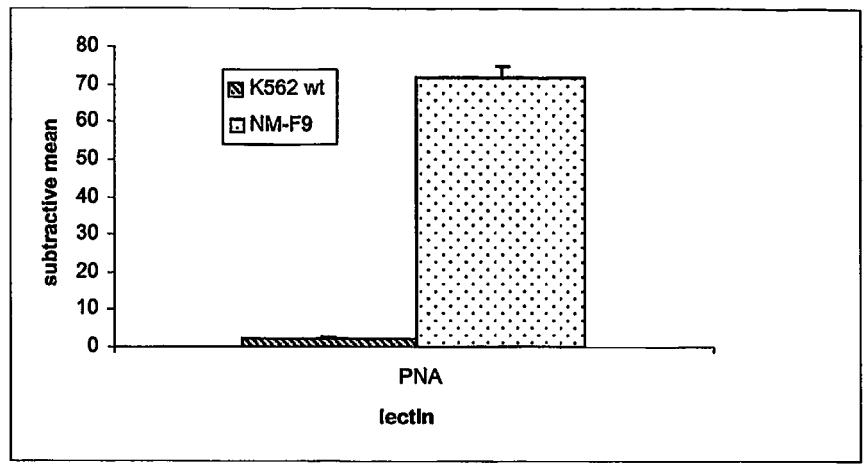
Figure 3:
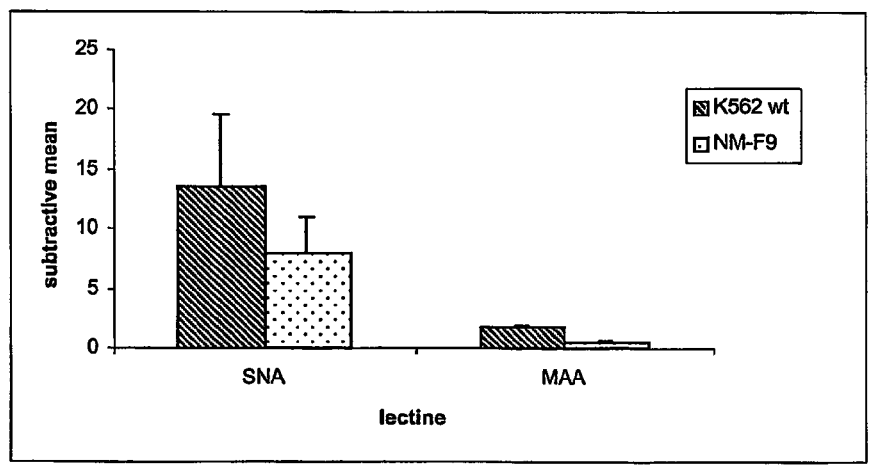
Figure 3:
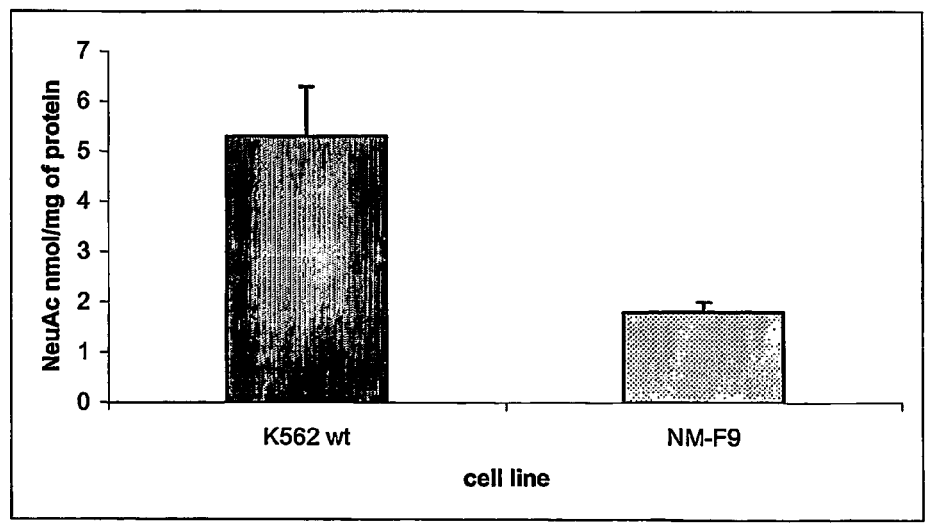

FIG. 3: Reduced sialylation on NM-F9 cells compared with wild type cells. A, Sialic acids glycosidic bound in alpha 2-3 and 2-6 on membrane proteins and lipids are stained preferentially by the lectins MAA and SNA, respectively. The lectin PNA binds preferentially the TF carbohydrate and not the sialylated TF (product information from Vector Laboratories). Staining was analysed by flow cytometry. B, In membrane fractions of NM-F9 and K562-wt cells the sialic acid content was determined using the thiobarbiture acid assay.

Figure 4:
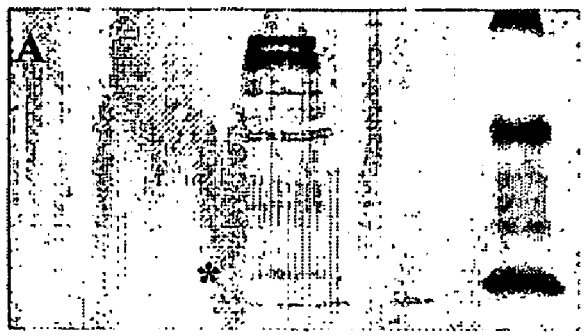
Figure 4:
Figure 4:

FIG. 4 Glycophorin A carries the TF-antigen in NM-F9 cells. Membrane lysates of K562-wt and NM-F9 cells were separated by a 12% SDS polyacrylamide gel and blotted onto a membrane. TF (A) and AGPA (B) were detected by staining with mAb A78-G/A7 and mAb A63-C/A9, respectively. GPA and AGPA isolated from erythrocytes typically migrate in SDS-PAGE as monomer and multimers (Pahlsson et al. 1994). GPA and BSA were used as negative and AGPA as positive control for staining with both antibodies. The A78-G/A7 positive protein (A) that comigrated with the single major C/A9 positive protein (B) was marked by an asterix.

FIG. 5 Stimulation of T-cell proliferation with NM-F9 cell lysates. Differentiated and matured, irradiated human dendritic cells (DC) derived from peripheral blood monocytes or CD4+, CD8+ and total T-cells isolated from human PBMC were analysed for cell proliferation separately or after cocultivation. Only a marginal level of T-cell proliferation was observed except for cocultivated DC and CD4+ T-cells which resulted in T-cell proliferation probably due to a mixed lymphocyte reaction. However, when DC were loaded with the NM-F9 cell lysate prior to cocultivation with the three T-cell population, respectively, increased T-cell proliferation could be determined. For loading of the DC two ratios of K562 cell lysate to DC, 1:1 and 0.1:1, were tested. Both ratios were effective in stimulating T-cell proliferation; the 1:1 turned out to be more effective for CD4+ and total T-cell proliferation, while the 1:0.1 ratio seems to be more effective for CD8+ T-cell proliferation. T-cell proliferation was analysed by the BrdU assay.

FIG. 6 Activation of naïve CD8+ cells against MUC1 and AGPA with NM-F9 cell lysates. Immature NMDC11 were loaded with lysate from NM-F9 and further maturated to functional dendritic cells m-NMDC11 which present processed antigens. Loaded M-NMDC11 were incubated with CTL from a A2+ donor. T cells were restimulated once by m-NMDC11 loaded with NM-F9 lysate, MUC1 A2 peptide and AGPA, non-loaded m-NMDC11 were used controls. ELISPOT analysis measuring the INFa secretion was performed.

Figure 7:
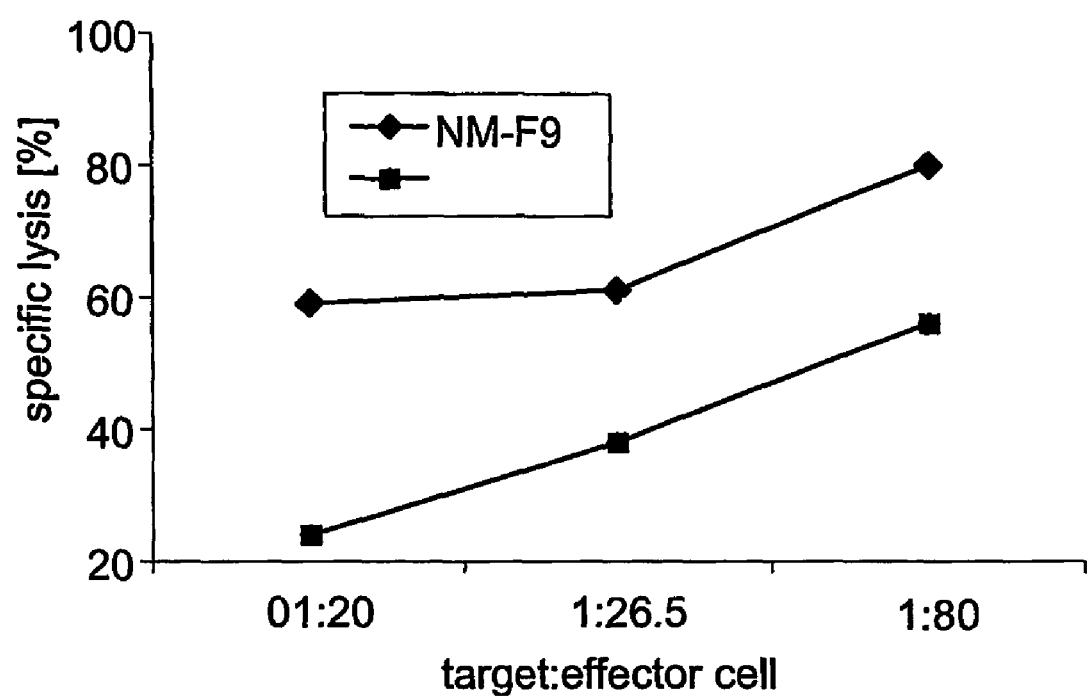

FIG. 7 NM-F9 cells are more efficiently lysed by natural killer cells than K562 wild type cells. NK cells were selected from PBMC and co-cultivated with NM-F9 or K562 wt as target cells in the indicated ratio.

The Examples illustrate the invention:

EXAMPLE 1

Cultivation of K562, NM-F9 and NM-D4 Cells

K562, NM-F9 and NM-D4 were cultured in RPMI 1640 supplemented with 10% FCS and 2 mM glutamine and grown at 37° C. in a humidified atmosphere of 6%, preferably of 8% $CO_2$.

EXAMPLE 2

Mutagenesis/Screening

A) Methods
A-1) Mutagenesis

Per sample K562 cells were washed in PBS and seeded at $10^6$ cells per ml cell culture medium supplemented with EMS (0.1 mg/ml, ethyl methanesulfonate, Sigma-Aldrich) overnight at 37° C. and 5% $CO_2$. Cells were washed and provided with fresh medium. Every second day cell vitality was determined by trypan blue staining and cells were analysed by immunocytochemical staining.

A-2) TF-selection: K562 cells were washed in B-PBS (0.5% BSA in PBS), incubated with 50 µl of supernatant of hybridoma cultures of mAb A78-G/A7 or PankoMab and 950 µl B-PBS at 4° C. for 30 min. After washing the procedure was repeated with 50 µl rat-anti-mouse-IgM-antibody or rat-anti-mouse-IgG-antibody conjugated with MicroBeads (Miltenyi Biotec, Köln, Germany). After washing the magnetically labelled TF-positive K562 cells were separated by two successive columns provided by Miltenyi (Köln, Ger) as described in the manufacturers manual. Following 9 days of cultivation, the isolation procedure was repeated in total three times. Finally, the isolated TF-positive K562 cells were cloned by limited dilution in 96-well plates (1 cell/100 µl).

A-3) MUC1-selection: As TF-selection with the exception that PankoMab and rat-anti-mouse-IgG-antibody conjugated with MicroBeads (Miltenyi Biotec, Köln, Germany) was used.

A-4) FACS Analysis (Flow Cytometry)

Antibody staining: About $3 \times 10^5$ cells were incubated at 4° C. for 1.5 h with primary mAb (hybridoma culture supernatants of A78-G/A7 (IgM), PankoMab (IgG1), all diluted 1:2 in cell culture medium) followed by the secondary Cy3-conjugated goat anti-mouse IgM or IgG antibody 1:200 in PBS at 4° C. for 30 min and washed again. Resuspended cells (200 µl PBS) were investigated by flow cytometry (flow cytometer: Coulter Epics, Beckman Coulter, Krefeld, Ger).

Quantitative analyses were carried out using the Expo32 software (Becton Coulter) with following parameter for antibody labelled cells: forward scatter (FS): 26 V, gain 1, sideward scatter (SS): 807 V, gain 5, FL2: 740 V, gain 1, and following parameter for lectin labelled cells: FS: 26 V, gain 1, SS: 807 V, gain 5, FL1:740 V, gain 1).

B) Results
B-1) Glycoengineering of K562 Cells

K562 wt cells were treated with EMS and used as non-treated cells and treated cells. TF-positive cells were selected using the TF-specific mAb A78-G/A7 coupled to magnetobeads (FIG. 1B: cells before separation). After three rounds of isolation a K562 cell population of 93% TF-positive cells was received. However, the percentage of TF-positive K562 cells decreased over time reaching a bottom level of about 20% TF-positive cells 14 days following the isolation procedure. For stable expression of the TF-positive phenotype K562 cells were isolated for a forth time and cloned thereafter by limited dilution. Among thirty K562 cell clones that were obtained thirteen cell clones expressed high amounts of the TF antigen and from these eight cell clones displayed a homogenous TF expression on the cell surface of the whole cell population (FIG. 1A). These cell clones stably expressed the TF antigen until now (about 12 month). Analysis by flow cytometry revealed approximately an 31-fold increase of the TF expression level for NM-F9 cells (FIG. 2) reflecting the strong expression of TF on this clone, also reflected by a subtractive mean in FACs analysis of about 48, which was chosen for further characterization. The necessity for cloning in order to obtain a stable TF-positive cell population is due to a higher proliferation rate of TF-negative cells which hence overgrow TF-positive clones over time, e.g. NM-F9 has a slower doubling rate than the TF-negative clone H9.

For the generation of a TF-positive clone which expresses more of the tumour-specific MUC1 epitope TA-MUC1, F9 cells were treated, selected and single cell cloned as described above using PankoMab for selection. The stable clone D4 was selected for further characterization due to its increased PankoMab staining in flow cytometry.

EXAMPLE 3

Characterization of the Cell Lines

A) Methods
A-1) Immunocytochemistry

About $5 \times 10^4$ cells/well were applied on multitest slides (Roth GmbH) and sedimented for 30 min at 37° C. plus 60 min at room temperature. After careful removal of the supernatant cells were dried and frozen overnight. The immunostaining was carried out as already described (19): Briefly, cells were fixed by 5% formaldehyde, washed with PBS, and incubated with hybridoma culture supernatants of the primary mAbs: A78-G/A7 (1:5), mAb A83-C/B12 (1:5), mAb A63-C/A9 (1:5), mAb PankoMab (1:5), or mAb HB-Tn1 (1:50) overnight at 4° C. After washing cells were incubated with the secondary antibody $Cy_3$-conjugated goat anti-mouse IgM (µ-chain specific) or IgG (Fc γ-fragment specific, 1:100 in PBS) for 30 min at 4° C. MAbs of different isotypes (mouse IgG1χ MOPC 21 and IgMχ TEPC 183) were used as negative controls. Multitest slides were covered with Mowiol mounting medium (10 M glycerol, 40% Mowiol 4-88 (Calbiochem), 0.2 M Tris buffer pH 8.5, 0.1% diazobicyclo-octane). Cy3-stained cells were visualized by fluorescence microscope Axioplan 2 (Zeiss, Oberkochem Ger) and pictures documented by using software Axiovision 3.1.

A-2) Flow Cytometry (FACS)

Antibody staining: About $3 \times 10^5$ cells were incubated at 4° C. for 1.5 h with primary mAb (hybridoma culture supernatants of A78-G/A7, A83-C/B12, A63-C/A9, PankoMab, all diluted 1:2, or mAb HB-Tn1 and anti-CD15 diluted 1:20, or anti-Sialyl-Lewis$^x$ diluted 1:100 in cell culture medium) followed by the secondary Cy3-conjugated goat anti-mouse IgM or IgG antibody 1:200 in PBS at 4° C. for 30 min and washed again. Resuspended cells (200 µl PBS) were investigated by flow cytometry (flow cytometer: Coulter Epics, Beckman Coulter, Kreefeld, Ger).

Lectin staining: After washing twice with PBS and once with HBSS with 4% BSA (Hanks' Balanced Salt) cells were incubated with FITC-conjugated PNA (1:400), FITC-conjugated SNA (1:50), or FITC-conjugated MAA (1:50) in HBSS/4% BSA at 4° C. for 1 h. After washing cell pellets were resuspended in 200 µl HBSS/4% BSA for analysis.

Quantitative analyses were carried out using the Expo32 software (Beckman Coulter) with following parameter for antibody labelled cells: forward scatter (FS): 26 V, gain 1, sideward scatter (SS): 807 V, gain 5, FL2: 740 V, gain 1, and following parameter for lectin labelled cells: FS: 26 V, gain 1, SS: 807 V, gain 5, FL1:740 V, gain 1).

A-3) Scatchard Analysis

PankoMab was chelated with p-SCN-Benzyl-DTPA and radiolabelled with $^{111}$In according to Nikula et al. (T. K. Nikula, M: J: Curcio, M. W. Brechbiel, O. A. Gansow, R. D. Finn, D. A. Scheinberg Nucl. Med. Biol. 22(3), 387-390 (1995). Labelling was done with carrier-free $^{111}$In to specific activities of 7-37 MBq/mg. Binding assay was performed in duplicates with $1\times10^6$ cells of K562, NM-D4 and NM-F9 in 1.5 ml Eppendorf tubes and increasing serial dilutions of labelled antibody (320 ng-5 ng) in a total volume of 200 µl PBS supplemented with 1% BSA to avoid non-specific binding. Cells were incubated for 1 hour at 4-8° C., separated from unbound antibody by centrifugation at 4000 rpm for 3 minutes and washed 2 times with 200 µl PBS/1% BSA. Cell bound radioactivity was quantified in a gamma-counter. Comparability of immunoreactivity of labelled and unmodified PankoMab was confirmed by competition of $^{111}$In-PankoMab with Pankomab using the same experimental protocol. 5 ng $^{111}$In-PankoMab was added to increasing amounts of PankoMab and incubated with the cells. PankoMab binding affinitiy and capacity were calculated for each individual experiment by scatchard analysis.

A-4) Generation of Membrane Lysate

Membrane lysates were generated as already described (Vachon L. Costa T. and Hetz A. GTPase and adenylat cyclase desensitise at different rates in NG108-15 cells. Mol. Pharmacol., 31, 159-168 (1987)) with following modifications: $2.2\times10^8$ cells were lysed by freeze/thawing in liquid nitrogen for 3 times. After addition of 7.5 ml hypotonic buffer (5 mM Tris/HCl, pH 7.6, 1 mM EGTA, 5 mM $MgCl_2$, 10 µg/ml leupeptin, 250 µmol PMSF) the resuspended cell sediment was centrifuged at 1000×g for 10 min at 4° C. The pellet was resuspended and centrifuged again at 1000×g for 10 min at 4° C. Supernatants of both centrifugation steps were combined and membrane isolation was carried out by centrifugation at 25000×g for 20 min at 4° C. The pellet was resuspended in 5 ml homogenization buffer (50 mM Tris/HCl, pH 7.6, 1 mM EGTA, 5 mM $MgCl_2$, 10 µg/ml leupeptin, 250 µmol PMSF) and centrifuged again at 25000×g for 20 min at 4° C. Asialoglycophorin A was isolated from the homogenized membranes as already described before (Pahlsson P, Douglas P, Blackall M. U., Biochemical, charakterization of the O-glycans on recombinant glycophorin A expressed in Chinese hamster ovary cells, Glycoconjugate Journal 11: 43-50, (1994)) using nonidet-lysis buffer. The resulting clarified lysate was used for immunoblot analyses.

A-5) Immunoblot Analyses

Membrane lysates were boiled in Laemmli SDS-PAGE buffer, separated by SDS-PAGE (12%) and transferred onto nitrocellulose membrane as described elsewhere (Goletz S, Hanisch F G, Karsten U. Novel alphaGalNAc containing glycans on cytokeratins are recognized invitro by galectins with type II carbohydrate recognition domains. J Cell Sci 1997 July; 110 (Pt 14):1585-96)). Membranes were blocked with 3% BSA in TBS/0.1% Tween and incubated with the primary mAb A78-G/A7 (1:5) or A63-C/A9 (1:5) overnight and alkaline peroxidase conjugated secondary antibody (goat anti-mouse IgM, µ-chain-specific (1:5000)) at 37° C. for 1 h. Staining was performed using NBT and BCIP detection as in (Goletz S, Hanisch F G, Karsten U. Novel alphaGalNAc containing glycans on cytokeratins are recognized invitro by galectins with type II carbohydrate recognition domains. J Cell Sci 1997 July; 110 (Pt 14):1585-96)).

A-6) ELISA

ELISA 1: 96-well microtiter plates were coated with purified mAb PankoMab (0.1 µg/well; IgG1) overnight at 4° C. in PBS. Blocking of the wells was performed with 5% BSA and washing steps with 0.1% Tween 20 in PBS. In successive incubation steps cellular supernatant (before and after treatment with sialidase, as described above) was added first, then supernatants of mAb A78-G/A7 (1:200, IgM) or mAb clone HB-Tn1 (1:1000, IgM), and followed by peroxidase-conjugated goat anti-mouse IgM-antibody, µ-chain-specific (1:5000). All incubation steps were performed for 1.5 h at room temperature and combined with intensive washing steps in between. The TF-positive or Tn-positive MUC1 antigen-antibody-complexes were stained by o-phenylendiamin as described in (Goletz S, Hanisch F G, Karsten U. Novel alphaGalNAc containing glycans on cytokeratins are recognized invitro by galectins with type II carbohydrate recognition domains. J Cell Sci 1997 July; 110 (Pt 14):1585-96)) and detected by ELISA-reader dual at 492 nm/620 nm (ELISA-Reader, Dynax Technologies, Philadelphia, USA).

ELISA 2: as ELISA 1, except: 96 well flat bottom plates (TPP, Trasadingen, Switzerland) were coated with 0.1 µg/well TF-PAA, Tn-PAA, or AGPA, or MUC1 purified from supernatants of NM-F9 cells (1:40; optimal MUC1 dilution was determined with anti-MUC1-antibody A76-A/C7, preferably, however with PankoMab), each diluted in PBS. Mice sera were incubated for 2 h. PankoMab (1:500), A78-G/A7 (1:500) and Tn-HB1 (1:500) were used as positive controls. For negative control the mice serum was replaced by medium. Peroxidase-labelled rabbit anti-mouse IgG or for the positive controls anti-mouse IgM (1:5000) were used as secondary reagent.

ELISA 3: as ELISA 2, except that the POD-labelled anti-human IgG antibody was used and diluted 1:10,000.

A-7) Determination of Membrane Glycoconjugate-Bound Sialic Acids

Isolation of membrane glycoconjugate-bound sialic acids was performed as already described (Mantey L. R., Keppler O. T., Pawlita M., Reutter W., Hinderlich S. Efficient biochemical engineering of cellular sialic acids using an unphysiological sialic acid precursor in cells lacking UDP-N-acetylglucosamine 2-epimerase. FEBS Letters 503: 80-84 (2001)) by lysing $10^7$ cells in lysis buffer in combination with needle sheering. After centrifugation pellets were resuspended and hydrolyzed in acetic acid. Determination of membrane glycoconjugate-bound sialic acid was performed by thiobarbituric acid method (Aminoff D. Methods for the quantitative estimation of N-acetylneuraminic acid and their application to hydrolysates of sialomucoids. Biochem. Journal 81: 384-392 (1961)).

B) Results

B-1) Cell Surface Expression of TF and TF-Bearing Proteins

B-2) Characteriztion of NM-F9 and NM-D4

TF which is absent on K562 is strongly and stably expressed on NM-F9 and NM-D4 as shown by binding of the TF specific antibodies A78-G/A7, Nemod-TF1 and Nemod-TF2. Neuramidase treatment of strongly TF-positive NM-F9 reveals that sialylation is largely reduced but some TF is still sialylated (FIG. 2). The latter fact is depending on media conditions.

NM-F9: Beside the very strong expression of TF, Tn and Sialyl-Tn, which are both weakly expressed in K562 wt (K562 wild type; equals K562 as obtained from DSMZ), are up-regulated and down-regulated, respectively. (FIGS. 1A-D and FIG. 2) To determine whether increased carrier protein expression was in part responsible for these changes in TF expression, the expression of glycophorin A (GPA) and MUC1, major known carriers for TF, were analysed. Clearly, no different expression level was seen for MUC1 and only a minor increase in GPA (FIG. 1E, F, I, J and FIG. 2). In contrast, the binding of the antibody A63-C/A9, which recognizes glycophorin A only if glycosylated with TF at a certain site therefore acting as a marker for asialoglycophorin A (AGPA), the TF glycosylated version of GPA, is very strong on NM-F9 and is not above background in K562 wt (FIG. 1G, H). These results indicate that the increased TF expression on NM-F9 is caused by a strongly reduced ability of the cell to sialylate which is supported by the binding studies with the lectins SNA, PNA and MAA (FIG. 3A) and the determination of the sialic acid content in the membrane fraction of K562 wt and NM-F9 cells (FIG. 3B). Lectin staining with MAA and SNA revealed that the total amount of α2-3- and 2-6-linked sialic acids on membrane proteins and lipids was about five-fold and two-fold, respectively, lower in NM-F9 cells (FIG. 3A). Binding of the sialylation-sensitive lectin PNA which preferentially binds to TF but also other desialylated terminal galactose residues increased about 33-fold in NM-F9 (FIG. 3A). Finally, the chemically determined content of sialic acids in the cell membrane was almost three-fold reduced in NM-F9 (FIG. 3B).

Interestingly, $Le^x$, a complex carbohydrate tumour marker on N- and O-glycans, was present on K562-wt cells (i.e. K562 wildtype cells as for example provided by the DSMZ) but its synthesis was strongly induced in NM-F9 cells (FIG. 2). However, the sialylated form of $Le^x$ (s-$Le^x$), as well as other Lewis carbohydrate antigens (i.e. $Le^a$, s-$Le^a$, $Le^y$), were absent in K562-wt and NM-F9 cells. UEAI, which detects terminal fucose in various linkages including fucose on $Le^x$ and $sLe^x$, did only weakly bind to K562 wt but strongly to NM-F9. This assumes that the increased $Le^x$ is generated by an up-regulation of fucosylation which was not further investigated.

NM-D4: The clone NM-D4 has similar properties as NM-F9. They show a very similar expression of, for example TF and $Le^x$ (very strong), GPA (strong), and Sialyl-Tn and $sLe^x$ (very low or lacking). Differences are seen in a strong increase in TA-MUC1 and some decrease in Tn and the A63-C/A9 epitope, whereby the latter is still strongly expressed on NM-D4. In order to see if the number of TA-MUC1 epitopes on membrane bound MUC1 are increased, the number of binding sites of PankoMab on K562 wt, NM-F9 and NM-D4 and the affinity of the binding was determined by Scatchard analysis using radiolabelled $^{111}$In-PankoMab (table 1). Scatchard analysis allows the determination of the maximum number of antibody molecules bound per cell and the apparent association constant of the binding reaction. Plotting the ratio of specifically bound and free antibody against the concentration of specifically bound antibody reveals a straight line. The binding capacity per cell was calculated from the intercept value at the abscissa and the association constant from the slope of the line. Surprisingly, the number of binding sites of PankoMab was not elevated in NM-F9 or NM-D4. On the contrary, NM-D4 and NM-F9 have about 60-65% of the number of binding sites as K562 wt. However, the affinity of the interaction between PankoMab and the cells was changed. While PankoMab recognizes MUC1 on NM-F9 with only a slight increase in affinity, MUC1 on NM-D4 is recognized with a 5 times increased affinity compared to MUC1 on K562 wt. This reflects that the altered truncated glycosylation leads to a better accessibility and/or folding of the complex carbohydrate-induced conformational tumour epitope of MUC1 (TA-MUC1) which is more prevalent in NM-D4 than in NM-F9. These determinations also show that MUC1, including TA-MUC1 is present on NM-F9, NM-D4 and K562 wt with an amount of antibody binding sites between about $1$-$1.5*10^5$, which is not low and contradicts the non- or hardly detectable amounts of MUC1 on K562 wt reported earlier (Zhang K, Sikut R, Hansson G C. A MUC1 mucin secreted from a colon carcinoma cell line inhibits target cell lysis by natural killer cells. Cellular Immunology, 1997; 176:158-165).

B-3) Identification of TF-Glycosylated Proteins

Asialoglycophorin A: The binding of A63-C/A9 shows that TF is present on GPA. A63-C/A9 recognizes specifically a mixed carbohydrate-peptide epitope of a certain TF on the extracellular portion of GPA (data not shown, manuscript in preparation). The 12-fold increased binding of A63-C/A9 on NM-F9 (FIG. 1G, H and FIG. 2) and its only very slight increase in binding after treatment of the cells with neuraminidase (FIG. 2) assumes that GPA of NM-F9 is almost free of sialic acids and most of the 15 TF groups exposed resembling asialoglycophorin A (AGPA). This was confirmed by Western blot analyses of membrane lysates where, in contrast to K562 wt cells, many membrane-bound TF-positive proteins could be detected in NM-F9 cells by A76-G/A7 staining (FIG. 4A), including GPA via comigration with a single major protein that could be stained with A63-C/A9 (FIG. 4B). The electrophoretic mobility of the A63-C/A9-positive protein resembled that of the desialylated monomer of AGPA generated from erythrocytes with an apparent and theoretical molecular weight of 24 kDa.

Secretory MUC1: MUC1 is not only expressed on the cell surface but also secreted into the cell culture supernatant (table 2). Secretory MUC1 from NM-F9 and NM-D4 is positive for TF whereby MUC1 from NM-D4 carries more TF than from NM-F9. MUC1 from K562 wt is negative and can only reach a TF level comparable to NM-F9 after neuraminidase treatment. In contrast, MUC1 secreted by ZR75—1 cells, which are known to secrete high amounts of MUC1, is TF-negative and even when treated with neuraminidase only low amounts of TF-positive MUC1 could be detected, although ZR75-1 cells are TF-positive even without neuraminidase treatment (results not shown). The MUC1 from NM-D4, caught by the glycosylation independent HMFG-1, shows also an increased PankoMab binding compared to K562 wt and NM-F9 (table 2).

EXAMPLE 4

Stimulation of Immune Reactions In Vitro and In Vivo

A) Methods:
A-1) T Cell Proliferation Assay

Immature human dendritic cells were prepared by differentiation of monocytes (hmoDC) using the method of Romani (Romani N, Gruner S, Brang D, Kampgen E, Lenz A, Trockenbacher B, Konwalinka G, Fritsch P O, Steinman R M, Schuler G. Proliferating dendritic cell progenitors in human blood. Journal of Experimental Medicine 180: 83-93 (1994)). Peripheral blood monocytes were isolated from peripheral blood of healthy human donor by Ficoll gradient centrifugation. Adherent cells which adhere on plastic were cultured for 6 days in RPMI-1640, 10% FCS, 1000 U/ml GM-CSF (Leukomax; Novatis Pharma GmbH, Nurnberg, Ger), 2.5 ng/ml TNFα and 1000 U/ml IL-4 (both PreproTech EC, London, UK). The immature DC ($10^6$ cells/sample) were incubated 1:1 overnight with tumour cell lysates, which were obtained from $5 \times 10^6$ K562-F9 cells incubated at 46° C. for 22 h prior to freeze/thaw-lysis in liquid nitrogen. After washing the dendritic cells with sterile PBS and 75 ng/ml TNFα were added. After 2 days the mature hmoDC became CD14−, CD1a+, CD80hi, CD86hi, CD40hi, MHCIIhi, CD83hi, DC-Sign+ (flow cytometry using according antibodies at 1:20 in PBS, suffix: −=no expression, hi=high expression, +=positive expression). Prior to T cell sensitisation, the antigen loaded hmoDC were irradiated with 30 Gy.

T-cells were isolated from the non-adherent fraction of PBMC of healthy HLA-A2 positive donor by a column of nylon wool (Polysciences Inc., Eppelheim, Ger). Alternativaly, CD4+ or CD8+ T-cells were isolated from PBMC by CD4+ or CD8+ T-cell-MACS-Isolationkits according to manufacturer's specifications (Miltenyi). Total T-cells, CD4+ or CD8+ T-cells were incubated in serum-free media (AIM-V medium) with mature hmoDC loaded 1:1 with cell lysate. The ratio of responder to stimulator (T-cell:DC) was 10:1. After overnight incubation 10 U/ml IL-2, 1.5 U/ml IL-1β and 5 ng/ml IL-7 were added. After incubation for four days T-cells were restimulated by mature hmoDC loaded with cell lysate. T-cell proliferation was analysed by the BrdU assay.

BrdU was incorporated into proliferating T-cells according to manufacturers protocol (Roche Diagnostik GmbH, Mannheim, Ger). After fixing, the cells were incubated with POD-labelled anti-BrdU-antibody. The subsequent staining reaction was stopped by 1 M sulfuric acid. Detection of antibody labelling was achieved by photometry at an optical density of 450 nm (Ref. 690 nm).

A-2) Activation of Naïve CD8+ Cells Against MUC1 and AGPA with NM-F9 Cell Lysates Immature NMDC11 are optimized MUTZ-3 derived cells which are fully functional human dendritic cells displaying features as described in PCT/EP02/09260 in the immature state. Immature NMDC11 are generated and further matured as described for MUTZ-3 in PCT/EP02/09260. MUTZ-3 can also be used in these assays albeit with a lower effectivity. Immature NMDC11 were loaded with lysates from F9 and further matured to functional dendritic cells m-NMDC11 which present processed antigens. Loaded M-NMDC11 were incubated with CTL from a A2+donor. T cells were restimulated once by m-NMDC11 loaded with F9 lysate, MUC1 A2 peptide and AGPA, non-loaded m-NMDC11 were used controls. ELISPOT analysis measuring the INFgamma secretion was performed.

A-3) Vaccination of NMRI and NOD/SCID Mice

NMRI mice were immunized and boostered 2 weeks later subcutaneously with lysates of temperature-treated K562 cells ($5 \times 10^6$ cells/mouse) and incomplete Freund's adjuvant. One day before immunization and 9 and 27 days after immunization mice were bled to analyze the serum for TF-, Tn-, MUC1 and asialoglycophorin A antibodies by ELISA 2.

A human immune system is established by intraperitoneal application of human peripheral blood lymphocytes into NOD-SCID mice irradiated one day earlier (PBL, standard preparation, $5 \times 10^7$ cell/mouse). 2-4 h after application of PBL, mice were immunized subcutaneously and boostered as described aboved. Cell lysates of Mel624 cells ($5 \times 10^6$ cells/mouse) were used as negative control. For analysis of the sera, mice were bled at days 13 and 28 after the first immunization. The analyzes were carried out by ELISA 3.

B) Results:

B-1) Induction of Cellular and Humoral Immune Responses

In order to investigate the potential of NM-F9 lysates to induce cellular and humoral immune responses following assays were performed: It could be shown in vitro that T-cell proliferation was induced when cocultivated with mature monocyte derived DC loaded with NM-F9 cell lysates (FIG. 5). The DC were loaded with the lysate in the immature state and further maturated which leads to antigen uptake, processing and presentation in the context of MHC class I and II molecules on mature DC (hmoDC). This immunogenic effect of NM-F9 cell lysates was observed for total T-cells, CD4+ T helper cells and cytotoxic CD8+ T-cells.

MUC1 obtained from NM-D4 by purification from the supernatant using PankoMab for immunopurification did not show an immunoinhibitory effect on the T cell proliferation measured by BrdU-Assay in an experiment which was performed similar as the experiment in PCT/EP03/08014 example 5B) but using MUC1 purified from NM-D4.

Activation of specific naïve cytotoxic T cells against MUC1 and AGPA were tested with functional mature human dendritic cells m-NMDC11 loaded with NM-F9 lysates in the prime reaction and restimulation with m-NMDC11 loaded with a MUC1 A2 peptide and AGPA protein respectively, showing that naïve CTL can be activated against these antigens using NM-F9 (FIG. 6).

Induction of an antibody response towards the several antigens was tested in NMRI mice and in NOD/SCID mice reconstituted with human PBMC that were vaccinated with NM-F9 cell lysates. An antibody response in form of murine and human IgG (table 3) could be observed against TF, Tn, MUC1 and AGPA in NMRI and reconstituted NOD-SCID, respectively. The induction of an IgG response indicates a switch of antibody class associated with a T helper cell immune response as well as induction of memory immune responses against the above antigens.

EXAMPLE 5

NM-F9 Cells are More Sensitive to Cell Lysis by Natural Killer Cells than the K562 Wild Type Cells K562 cells are well-known target cells for cell lysis by natural killer (NK) cells. Although this phenomenon is described in many publications the molecular mechanism(s) and targets on K562 cells remain still to be elucidated (Voshol et al. Glycobiology 1993). The effect of glycostructures, e.g. sialic acids, on the surface of K562 cells onto cell lysis by NK cells is discussed very controversly (Voshol et al. Glycobiology 1993). In a very early publication (Werkmeister et al. Int. J. Cancer 1983) the authors described an increase in NK cell sensitivity of K562 cells when treated with neuraminidase which eliminates sialic acids on the cell surface. This observation could not be confirmed by others in similar assays (Dall'Olio et al. Glycobiology 1997, el Ouagari et al. J. Biol. Chem. 1995). On the contrary, by addition of sialic acids conjugated to various carriers lysis of K562 cells was inhibited (Van Rinsum et al. Int. J. Cancer 1986) suggesting that the presence of sialic acids is a prerequisite for cell lysis. Moreover, in two very recent publications (Ohyama et al. Embo J. 1999; Ohyama et al. Proc. Natl. Acad. Sci. 2002) it was shown that hypersialylated cells are better target cells for NK cell lysis than hyposialylated cells. The authors identified the sialylated form of the Lewis X antigen (sLe$^x$) as carbohydrate on target cell that is recognized by CD94 on NK cells mediating the NK cell sensitivity. Cell lysis is inhibited in presence of anti-sLe$^x$ antibodies but not in presence of antibodies recognizing Le$^x$ (the unsialylated form of the Lewis antigen).

With NM-F9 and -D4 cells we have two cell clones at hand that differ from K562 wild type cells by a very low degree of sialylation on the cell surface. To elucidate whether these differences in phenotype result in changed biological activities, we performed cytotoxicity assays with NK cells and NM-F9 as well as K562 wild type cells as target cells.

About $8 \times 10^6$ NK cells were isolated from $2 \times 10^8$ peripher blood monocytes (PBMC) by using anti-CD3 microbeads (Miltenyi Biotec, Germany) according to the manufacturer and additional cultivation overnight to eliminate the adherent monocytes. Next day, the presence of NK cells was confirmed by co-staining of the cells with PE-conjugated anti-CD56 and FITC-conjugated anti-CD16 antibodies and analysis by flow cytometrie (Coulter Epics, Beckman/Coulter). Immunostaining of cells for flow cytometry was described above. Analysis of NK cells by flow cytometry was performed with a forward scatter of 55 volt and gain 2, a sideward scatter of 400 volt and gain 20, in the FL1 channel (FITC, 650 volt, gain 1) and the FL2 channel (PE, 750 volt, gain 1) and a FL1-FL2 compensation of 3.8 and a FL2-FL1 compensation of 3.4. Usually, about 20% of the isolated cells were CD56+, CD16+ NK cells.

To analyse cytotoxicity of the NK cells an Europium release assay was performed as described earlier (Blomberg et al. J. Immunol. Methods 1986). Briefly, about $5 \times 10^6$ vital target cells were washed once with ice cold RPMI medium (RPMI 1640 with 5% fetal calf serum) and thereafter resuspended in 800 µl of an Europium buffer (pH 7.4) containing 50 mM HEPES, 93 mM NaCl, 5 mM KCl, 2 mM $MgCl_2$, 10 mM DTPA (Fluka, Germany), 2 mM Europium-III-acetat (Aldrich-Sigma, Germany). To transfer Europium$^{3+}$ ions into the target cells all the resuspended cells were electroporated (Multiporator, Eppendorf, Germany) in a 4 mm cuvette with one puls of 30 µs and 710 volt. Before and after electroporation cells are kept on ice for 6-10 min. Thereafter the cells are washed again for five times in the above mentioned ice cold cell culture medium and finally resuspended in cell culture medium (RPMI 1640, 10% fetal calf serum, 2 mM Glutamine) at a cell titer of $10^5$ cell per ml. For the cytotoxicity reaction $10^4$ target cells (100 µl) are given into a round-bottom-microtiterplate and incubated for 4 h at 37° C. in a $CO_2$ incubator with NK cells at the indicated target:effector ratio or for control without NK cells. Theraftrer, cells are spinned down (400×g, 5 min) and 20 µl of the cell culture supernatant is added to an enhancement solution (Perkin-Elmer, Germany) provided in a microtiterplate with flat bottom. Following 15 min of incubation at room temperature the release of Eu$^{3+}$ ions is detected in a time resolved fluorescence reader (Vector 2, Perkin-Elmer).

To determine the percentage of specific target cell lysis the percentage of specific Eu$^{3+}$ release is calculated as follows:

$$\% \text{ spontanous Eu}^{3+} \text{ release} = \frac{SR(\text{Counts}) - BR(\text{Counts})}{MR(\text{Counts}) - BR(\text{Counts})} \times 100$$

$$\% \text{ specific Eu}^{3+} \text{ release} = \frac{\text{effector/target Counts} - SR(\text{Counts})}{MR(\text{Counts}) - SR(\text{Counts})} \times 100$$

Where the spontanous and background Eu3+ release (SR) and (BR) correspond to the release after incubation of the target cells (SR) or just the cell culture supernatant of the target cells (BR) for 4 h at 37° C. without addition of NK cells. The maximal release (MR) from target cells is achieved by a 4 h incubation at 37° C. in presence of 50% ethanol. The sponanous and maximal releases were 1530±865 counts and 149861±16994 counts for NM-F9 cells and 10393±1856 counts and 237325±40542 counts for K562 wild type (wt) cells when BR was already subtracted. From that a % SR of 10.2%±4% for NM-F9 cells and 4.3%±0.3% for K562 wt cells was calculated, respectively, which is well under the limit of 30% SR for a successful assay. The assay was done in triplicate and repeated five times. The results presented in FIG. 7 demonstrate clearly that the hyposialylated NM-F9 cells differ from hypersialylated K562 wt cells in that they are much more sensitive to the cytolytic activity of NK cells than the K562 wt cells. Thus, the differences of NM-F9 and K562 wt cells that were observed for the phenotype as described above result in changed biological activities. The higher sensitivity of NM-F9 cells against NK cell cytotoxicity is in contrast to the literature where sialylated carbohydrates have been described to mediate the cytotoxic lysis by NK cells.

It is to be understood that this invention is not limited to the particular methodology, protocols and/or reagents as described herein as these may vary. It is also to be understood that the terminology used herein is for the purpose of describing particular embodiments only, and is not intended to limit the scope of the present invention which will be limited only by the appended claims.

TABLE 1

Scatchard analysis of the binding of the radiolabelled 111In-PankoMab to K562 wt, NM-F9 and NM-D4

|  | n | $K_{ass}$ | bindings sites/cell |
|---|---|---|---|
| K562wt | 3 | $1.8 * 10^8$ I/Mol | $1.5 * 10^5$ |
| NM-F9 | 4 | $2.2 * 10^8$ I/Mol | $0.9 * 10^5$ |
| NM-D4 | 12 | $9 * 10^8$ I/Mol | $1 * 10^5$ |

TABLE 2

In the supernatant of NM-F9 and NM-D4 cells the amount of secretory TF-positive MUC1 was increased. TF-positive MUC1 was detected by ELISA.

| | Catching mAb | | |
|---|---|---|---|
| | HMFG-1 | PankoMab | |
| | | Secondary mAb | |
| | | A-78-G/A7 | |
| Cell line | PankoMab | − sialidase | + sialidase |
| K562wt | + | − | + |
| NM-F9 | + | + | + |
| NM-D4 | ++ | ++ | ++ |

TABLE 3

Vaccination of NMRI and NOD/SCID mice with K562-F9 cell lysats.

| | mice with IgG immune response/total account of mice* | | | |
|---|---|---|---|---|
| mouse model | AGPA | TF | Tn | MUC1 |
| NMRI | 2/3 | 3/3 | 3/3 | 3/3 |
| NOD/SCID** | 3/3 | 3/3 | 3/3 | 3/3 |

*Three mice per group were vaccinated with the NM-F9 cell lysates and bleeded preimmunization and at day 9 and 27 (NMRI) or at day 13 and 28 (NOD/SCID) postimmunization for analysis of an IgG response against the indicated antigens. Mice with positive response showed at least a three-fold increase in antiserum titer compared with the preimmune serum (NMRI) or the 1st bleed.
**PBMC was injected before immunization

The invention claimed is:

1. A cell line which synthesizes and expresses on the cell surface mucin 1 (MUC1) and glycophorin comprising an exposed Thomsen-Friedenreich (TF) antigen, wherein the cell line is capable of inducing a humoral immune response against the exposed TF antigen.

2. The cell line of claim 1 which is selected from the group consisting of
   (a) a cell line denominated NM-F9 having the DSMZ accession number DSM ACC2606;
   (b) a cell line denominated NM-D4 having the DSMZ accession number DSM ACC2605; and
   (c) subclones of (a) or (b) which synthesizes and expresses on the cell surface mucin 1 (MUC1) and glycophorin comprising an exposed TF antigen, wherein the cell line is capable of inducing a humoral immune response against the exposed TF antigen.

3. The cell line of claim 1, comprising a vector which comprises a nucleic acid molecule.

4. The cell line of claim 3, wherein said nucleic acid molecule encodes at least one polypeptide of a polypeptide selected from the group consisting of a cytokine, MHC class I molecule, MHC class II molecule and costimulatory molecule, T cell epitope or multimers thereof, tumour antigen, hormone, sexual hormone, adjuvant, antibody or other molecules or fragments thereof having biological activity or any combination thereof.

5. A composition comprising a cell line which synthesizes and expresses on the cell surface mucin 1 (MUC1) and glycophorin comprising an exposed Thomsen-Friedenreich (TF) antigen, wherein the cell line is capable of inducing a humoral immune response against the exposed TF antigen.

6. The composition of claim 5, which is a pharmaceutical or vaccine composition.

7. The cell line of claim 1, wherein the glycophorin is asialoglycophorin.

8. The cell line of claim 1, wherein the MUC1 is tumor-associated MUC1 (TA-MUC1).

9. The cell line of claim 1, wherein the cell line is obtainable from the K562 cell line.

10. The cell line of claim 1, wherein the cell line is obtainable by chemical mutagenesis.

11. The cell line of claim 10, wherein the chemical mutagen is ethyl methanesulfonate (EMS).

12. The cell line of claim 1, wherein the cell line is further capable of inducing a humoral immune response against MUC1 and asialoglycophorin.

13. The cell line of claim 1, wherein the cell line is capable of inducing the humoral immune response against TF antigen in NMRI and/or NOD/SCID mice when administered at a dose of $5 \times 10^6$ cells/mouse.

* * * * *